(12) United States Patent
Kieval et al.

(10) Patent No.: US 8,290,595 B2
(45) Date of Patent: Oct. 16, 2012

(54) METHOD AND APPARATUS FOR STIMULATION OF BARORECEPTORS IN PULMONARY ARTERY

(75) Inventors: Robert S. Kieval, Medina, MN (US);
Peter T. Keith, Lanesboro, MN (US);
David J. Serdar, Shorewood, MN (US);
Bruce Persson, Shoreview, MN (US)

(73) Assignee: CVRx, Inc., Minneapolis, MN (US)

( * ) Notice: Subject to any disclaimer, the term of this patent is extended or adjusted under 35 U.S.C. 154(b) by 0 days.

(21) Appl. No.: 11/482,264

(22) Filed: Jul. 7, 2006

(65) Prior Publication Data
US 2007/0038259 A1 Feb. 15, 2007

Related U.S. Application Data

(63) Continuation of application No. 10/284,063, filed on Oct. 29, 2002, now Pat. No. 8,086,314.

(51) Int. Cl.
*A61N 1/05* (2006.01)
(52) U.S. Cl. ........................................... 607/44
(58) Field of Classification Search ...................... 607/44
See application file for complete search history.

(56) References Cited

U.S. PATENT DOCUMENTS

| | | | |
|---|---|---|---|
| 3,309,924 A | 3/1967 | Kolin | |
| 3,421,511 A | 1/1969 | Schwartz et al. | |
| 3,522,811 A | 8/1970 | Schwartz et al. | |
| 3,593,718 A | 7/1971 | Krasner et al. | |
| 3,645,267 A | 2/1972 | Hagfors | |
| 3,650,277 A * | 3/1972 | Sjostrand et al. | 607/44 |
| 3,835,864 A * | 9/1974 | Rasor et al. | 607/36 |
| 3,870,051 A | 3/1975 | Brindley | |
| 3,943,936 A | 3/1976 | Rasor et al. | |
| 4,014,318 A | 3/1977 | Dockum et al. | |
| RE30,366 E | 8/1980 | Rasor et al. | |
| 4,256,094 A | 3/1981 | Kapp et al. | |
| 4,323,073 A | 4/1982 | Ferris | |
| 4,331,157 A | 5/1982 | Keller, Jr. et al. | |
| 4,481,953 A | 11/1984 | Gold et al. | |
| 4,525,074 A | 6/1985 | Murakami | |
| 4,531,943 A | 7/1985 | Van Tassel et al. | |
| 4,551,862 A | 11/1985 | Haber | |
| 4,573,481 A | 3/1986 | Bullara | |
| 4,586,501 A | 5/1986 | Claracq | |
| 4,590,946 A | 5/1986 | Loeb et al. | |
| 4,628,942 A | 12/1986 | Sweeney et al. | |
| 4,640,286 A | 2/1987 | Thomson | |

(Continued)

FOREIGN PATENT DOCUMENTS

WO WO 93/02744 2/1993

(Continued)

OTHER PUBLICATIONS

Nishi et al. "Afferent Fibres From Pulmonary Arterial Baroreceptors in the Left Cardiac Sympathetic Nerve of the Cat," J. Physiol. 1974, 240, pp. 53-66.*

(Continued)

*Primary Examiner* — Eric D. Bertram
(74) *Attorney, Agent, or Firm* — Patterson Thuente Christensen Pedersen, P.A.

(57) ABSTRACT

Devices and methods for controlling the low-pressure baroreflex system for the treatment and/or management of cardiovascular, renal, and neurological disorders.

10 Claims, 18 Drawing Sheets

U.S. PATENT DOCUMENTS

| | | |
|---|---|---|
| 4,641,664 A | 2/1987 | Botvidsson |
| 4,664,120 A | 5/1987 | Hess |
| 4,682,583 A | 7/1987 | Burton et al. |
| 4,702,254 A | 10/1987 | Zabara |
| 4,709,690 A | 12/1987 | Haber |
| 4,711,251 A | 12/1987 | Stokes |
| 4,719,921 A | 1/1988 | Chirife |
| 4,739,762 A | 4/1988 | Palmaz |
| 4,762,130 A | 8/1988 | Fogarty et al. |
| 4,762,820 A | 8/1988 | Gavras |
| 4,770,177 A | 9/1988 | Schroeppel |
| 4,791,931 A | 12/1988 | Slate |
| 4,800,882 A | 1/1989 | Gianturco |
| 4,803,988 A | 2/1989 | Thomson |
| 4,813,418 A | 3/1989 | Harris |
| 4,819,662 A | 4/1989 | Heil, Jr. et al. |
| 4,825,871 A | 5/1989 | Cansell |
| 4,828,544 A | 5/1989 | Lane et al. |
| 4,830,003 A | 5/1989 | Wolff et al. |
| 4,832,038 A | 5/1989 | Arai et al. |
| 4,860,751 A | 8/1989 | Callaghan |
| 4,862,361 A | 8/1989 | Gordon et al. |
| 4,867,164 A | 9/1989 | Zabara |
| 4,881,939 A | 11/1989 | Newman |
| 4,886,062 A | 12/1989 | Wiktor |
| 4,887,608 A | 12/1989 | Mohl et al. |
| 4,915,113 A | 4/1990 | Holman |
| 4,917,092 A | 4/1990 | Todd et al. |
| 4,926,875 A | 5/1990 | Rabinovitz et al. |
| 4,930,517 A | 6/1990 | Cohen et al. |
| 4,934,368 A | 6/1990 | Lynch |
| 4,940,065 A | 7/1990 | Tanagho et al. |
| 4,960,129 A | 10/1990 | dePaola et al. |
| 4,960,133 A | 10/1990 | Hewson |
| 4,967,159 A | 10/1990 | Manes |
| 4,969,458 A | 11/1990 | Wiktor |
| 4,972,848 A | 11/1990 | Di Domenico et al. |
| 4,987,897 A | 1/1991 | Funke |
| 5,010,893 A | 4/1991 | Sholder |
| 5,025,807 A | 6/1991 | Zabara |
| 5,031,621 A | 7/1991 | Grandjean et al. |
| 5,040,533 A | 8/1991 | Fearnot |
| 5,078,736 A | 1/1992 | Behl |
| 5,086,787 A | 2/1992 | Grandjean et al. |
| 5,092,332 A | 3/1992 | Lee et al. |
| 5,111,815 A | 5/1992 | Mower |
| 5,113,859 A | 5/1992 | Funke |
| 5,113,869 A | 5/1992 | Nappholz et al. |
| 5,117,826 A | 6/1992 | Bartelt et al. |
| 5,134,997 A | 8/1992 | Bennett et al. |
| 5,144,960 A * | 9/1992 | Mehra et al. .................. 607/125 |
| 5,154,170 A | 10/1992 | Bennett et al. |
| 5,154,182 A | 10/1992 | Moaddeb |
| 5,158,078 A | 10/1992 | Bennett et al. |
| 5,170,802 A | 12/1992 | Mehra |
| 5,181,911 A | 1/1993 | Shturman |
| 5,199,428 A | 4/1993 | Obel et al. |
| 5,203,326 A | 4/1993 | Collins |
| 5,215,089 A | 6/1993 | Baker, Jr. |
| 5,222,971 A | 6/1993 | Willard et al. |
| 5,224,491 A | 7/1993 | Mehra |
| 5,243,980 A | 9/1993 | Mehra |
| 5,247,945 A | 9/1993 | Heinze et al. |
| 5,259,394 A | 11/1993 | Bens |
| 5,265,608 A | 11/1993 | Lee et al. |
| 5,269,303 A | 12/1993 | Wernicket et al. |
| 5,282,468 A | 2/1994 | Klepinski |
| 5,282,844 A | 2/1994 | Stokes et al. |
| 5,295,959 A | 3/1994 | Gurbel et al. |
| 5,299,569 A | 4/1994 | Wernicke et al. |
| 5,304,206 A | 4/1994 | Baker, Jr. et al. |
| 5,305,745 A | 4/1994 | Zacouto |
| 5,314,453 A | 5/1994 | Jeutter |
| 5,318,592 A | 6/1994 | Schaldach |
| 5,324,310 A | 6/1994 | Greeninger et al. |
| 5,324,325 A | 6/1994 | Moaddeb |
| 5,325,870 A | 7/1994 | Kroll et al. |
| 5,330,507 A | 7/1994 | Schwartz |
| 5,330,515 A | 7/1994 | Rutecki et al. |
| 5,331,966 A | 7/1994 | Bennett et al. |
| 5,335,657 A | 8/1994 | Terry et al. |
| 5,351,394 A | 10/1994 | Weinberg |
| 5,358,514 A | 10/1994 | Schulman et al. |
| 5,387,234 A | 2/1995 | Hirschberg |
| 5,408,744 A | 4/1995 | Gates |
| 5,411,535 A | 5/1995 | Fujii et al. |
| 5,411,540 A | 5/1995 | Edell et al. |
| 5,431,171 A | 7/1995 | Harrison et al. |
| 5,437,285 A | 8/1995 | Verrier et al. |
| 5,458,626 A | 10/1995 | Krause |
| 5,507,784 A | 4/1996 | Hill et al. |
| 5,509,888 A | 4/1996 | Miller |
| 5,522,854 A | 6/1996 | Ideker et al. |
| 5,522,874 A | 6/1996 | Gates |
| 5,529,067 A | 6/1996 | Larsen et al. |
| 5,531,766 A | 7/1996 | Kroll et al. |
| 5,531,778 A | 7/1996 | Maschino et al. |
| 5,531,779 A | 7/1996 | Dahl et al. |
| 5,535,752 A | 7/1996 | Halperin et al. |
| 5,540,734 A | 7/1996 | Zabara |
| 5,540,735 A | 7/1996 | Wingrove |
| 5,545,132 A | 8/1996 | Fagan et al. |
| 5,545,202 A | 8/1996 | Dahl et al. |
| 5,551,953 A | 9/1996 | Lattin et al. |
| 5,571,150 A | 11/1996 | Wernicke et al. |
| 5,575,809 A | 11/1996 | Sasaki |
| 5,578,061 A | 11/1996 | Stroetmann et al. |
| 5,593,431 A | 1/1997 | Sheldon |
| 5,634,878 A | 6/1997 | Grundei et al. |
| 5,643,330 A | 7/1997 | Holsheimer et al. |
| 5,645,570 A | 7/1997 | Corbucci |
| 5,651,378 A | 7/1997 | Matheny et al. |
| 5,680,590 A | 10/1997 | Parti |
| 5,683,430 A | 11/1997 | Markowitz et al. |
| 5,690,681 A | 11/1997 | Geddes et al. |
| 5,692,882 A | 12/1997 | Bozeman, Jr. et al. |
| 5,694,939 A | 12/1997 | Cowings |
| 5,695,468 A | 12/1997 | Lafontaine et al. |
| 5,700,282 A | 12/1997 | Zabara |
| 5,707,400 A | 1/1998 | Terry, Jr. et al. |
| 5,715,837 A | 2/1998 | Chen |
| 5,725,471 A | 3/1998 | Davey et al. |
| 5,725,563 A | 3/1998 | Klotz |
| 5,727,558 A | 3/1998 | Hakki et al. |
| 5,741,316 A | 4/1998 | Chen et al. |
| 5,741,319 A | 4/1998 | Woloszko et al. |
| 5,766,236 A | 6/1998 | Detty et al. |
| 5,766,527 A | 6/1998 | Schildgen et al. |
| 5,775,331 A | 7/1998 | Raymond et al. |
| 5,776,178 A | 7/1998 | Pohndorf et al. |
| 5,782,891 A | 7/1998 | Hassler et al. |
| 5,800,464 A | 9/1998 | Kieval |
| 5,807,258 A | 9/1998 | Cimochowski et al. |
| 5,810,735 A | 9/1998 | Halperin et al. |
| 5,814,079 A | 9/1998 | Kieval |
| 5,814,089 A | 9/1998 | Stokes et al. |
| 5,824,021 A | 10/1998 | Rise |
| 5,853,652 A | 12/1998 | Schildgen et al. |
| 5,861,012 A | 1/1999 | Stroebel |
| 5,861,015 A | 1/1999 | Benja-Athon |
| 5,876,422 A | 3/1999 | van Groeningen |
| 5,891,181 A | 4/1999 | Zhu |
| 5,895,416 A | 4/1999 | Barreas et al. |
| 5,904,708 A | 5/1999 | Goedeke |
| 5,913,876 A | 6/1999 | Taylor et al. |
| 5,916,239 A | 6/1999 | Geddes et al. |
| 5,919,220 A | 7/1999 | Stieglitz et al. |
| 5,928,272 A | 7/1999 | Adkins et al. |
| 5,938,596 A | 8/1999 | Woloszki et al. |
| 5,954,761 A | 9/1999 | Machek et al. |
| 5,967,986 A | 10/1999 | Cimochowski et al. |
| 5,967,989 A | 10/1999 | Cimochowski et al. |
| 5,987,352 A | 11/1999 | Klein et al. |
| 5,987,746 A | 11/1999 | Williams |
| 5,989,230 A | 11/1999 | Frassica |
| 5,991,667 A | 11/1999 | Feith |
| 6,006,134 A | 12/1999 | Hill et al. |

| | | | | | | |
|---|---|---|---|---|---|---|
| 6,016,449 A | 1/2000 | Fischell et al. | | 7,139,607 B1 | 11/2006 | Shelchuk |
| 6,023,642 A | 2/2000 | Shealy et al. | | 7,146,226 B2 | 12/2006 | Lau et al. |
| 6,050,952 A | 4/2000 | Hakki et al. | | 7,155,284 B1 | 12/2006 | Whitehurst et al. |
| 6,052,623 A | 4/2000 | Fenner et al. | | 7,158,832 B2 | 1/2007 | Kieval et al. |
| 6,058,331 A | 5/2000 | King | | 7,192,403 B2 | 3/2007 | Russell |
| 6,061,596 A | 5/2000 | Richmond et al. | | 7,194,313 B2 | 3/2007 | Libbus |
| 6,073,048 A * | 6/2000 | Kieval et al. .................... 607/17 | | 7,225,025 B2 | 5/2007 | Goode |
| 6,077,227 A | 6/2000 | Miesel et al. | | 7,228,179 B2 | 6/2007 | Campen et al. |
| 6,077,298 A | 6/2000 | Tu et al. | | 7,231,248 B2 | 6/2007 | Kramer et al. |
| 6,104,956 A | 8/2000 | Naritoku et al. | | 7,236,821 B2 | 6/2007 | Cates et al. |
| 6,106,477 A | 8/2000 | Miesel et al. | | 7,236,861 B2 | 6/2007 | Paradis et al. |
| 6,110,098 A | 8/2000 | Renirie et al. | | 7,286,878 B2 | 10/2007 | Stypulkowski |
| 6,115,628 A | 9/2000 | Stadier et al. | | 7,321,793 B2 | 1/2008 | Ben Ezra et al. |
| 6,115,630 A | 9/2000 | Stadier et al. | | 7,499,742 B2 | 3/2009 | Bolea et al. |
| 6,128,526 A | 10/2000 | Stadier et al. | | 7,616,997 B2 | 11/2009 | Kieval et al. |
| 6,141,588 A | 10/2000 | Cox et al. | | 7,623,926 B2 | 11/2009 | Rossing et al. |
| 6,141,590 A | 10/2000 | Renirie et al. | | 7,840,271 B2 | 11/2010 | Kieval et al. |
| 6,161,029 A | 12/2000 | Spreigl et al. | | 8,086,314 B1 | 12/2011 | Kieval |
| 6,161,047 A | 12/2000 | King et al. | | 2001/0003799 A1 | 6/2001 | Boveja |
| 6,178,349 B1 | 1/2001 | Kieval | | 2001/0020177 A1 | 9/2001 | Gruzdowich et al. |
| 6,178,352 B1 | 1/2001 | Gruzdowich et al. | | 2001/0023367 A1 | 9/2001 | King et al. |
| 6,193,996 B1 | 2/2001 | Effing et al. | | 2002/0005982 A1 | 1/2002 | Borlinghaus |
| 6,205,359 B1 | 3/2001 | Boveja | | 2002/0016548 A1 | 2/2002 | Stadler et al. |
| 6,206,914 B1 | 3/2001 | Soykan et al. | | 2002/0026228 A1 * | 2/2002 | Schauerte .................... 607/122 |
| 6,208,894 B1 | 3/2001 | Schulman et al. | | 2002/0058877 A1 | 5/2002 | Baumann et al. |
| 6,231,516 B1 | 5/2001 | Keilman et al. | | 2002/0068897 A1 * | 6/2002 | Jenkins et al. ............. 604/96.01 |
| 6,253,110 B1 | 6/2001 | Brabec et al. | | 2002/0072776 A1 | 6/2002 | Osorio et al. |
| 6,255,296 B1 | 7/2001 | Daniels | | 2002/0072782 A1 | 6/2002 | Osorio et al. |
| 6,266,564 B1 | 7/2001 | Hill et al. | | 2002/0103516 A1 | 8/2002 | Patwardhan et al. |
| 6,292,695 B1 | 9/2001 | Webster, Jr. et al. | | 2002/0107553 A1 | 8/2002 | Hill et al. |
| 6,292,703 B1 | 9/2001 | Meier et al. | | 2002/0128700 A1 | 9/2002 | Cross, Jr. |
| 6,324,421 B1 | 11/2001 | Stadier et al. | | 2002/0143369 A1 | 10/2002 | Hill et al. |
| 6,341,236 B1 | 1/2002 | Osorio et al. | | 2002/0151051 A1 | 10/2002 | Li |
| 6,371,922 B1 | 4/2002 | Baumann et al. | | 2002/0165586 A1 | 11/2002 | Hill et al. |
| 6,393,324 B2 | 5/2002 | Gruzdowich et al. | | 2002/0183791 A1 | 12/2002 | Denker et al. |
| 6,397,109 B1 | 5/2002 | Cammilli et al. | | 2003/0040785 A1 | 2/2003 | Maschino et al. |
| 6,401,129 B1 | 6/2002 | Lenander | | 2003/0050670 A1 | 3/2003 | Spinelli et al. |
| 6,415,183 B1 | 7/2002 | Scheiner et al. | | 2003/0060848 A1 | 3/2003 | Kieval et al. |
| 6,438,409 B1 | 8/2002 | Malik et al. | | 2003/0060857 A1 | 3/2003 | Perrson et al. |
| 6,438,428 B1 | 8/2002 | Axelgaard et al. | | 2003/0060858 A1 | 3/2003 | Kieval et al. |
| 6,442,413 B1 | 8/2002 | Silver | | 2003/0078623 A1 | 4/2003 | Weinberg et al. |
| 6,442,435 B2 | 8/2002 | King et al. | | 2003/0093130 A1 | 5/2003 | Stypulkowski |
| 6,445,953 B1 | 9/2002 | Bulkes et al. | | 2003/0100924 A1 | 5/2003 | Foreman et al. |
| 6,473,644 B1 | 10/2002 | Terry et al. | | 2003/0120316 A1 | 6/2003 | Spinelli et al. |
| 6,522,926 B1 | 2/2003 | Kieval et al. | | 2003/0149450 A1 | 8/2003 | Mayberg |
| 6,564,101 B1 | 5/2003 | Zikria | | 2003/0212440 A1 | 11/2003 | Boveha et al. |
| 6,564,102 B1 | 5/2003 | Boveja | | 2003/0229380 A1 | 12/2003 | Adams et al. |
| 6,584,362 B1 | 6/2003 | Scheiner et al. | | 2004/0010303 A1 | 1/2004 | Bolea et al. |
| 6,600,956 B2 | 7/2003 | Maschino | | 2004/0019364 A1 | 1/2004 | Kieval et al. |
| 6,611,713 B2 | 8/2003 | Schaurte | | 2004/0034391 A1 | 2/2004 | Baumann et al. |
| 6,622,041 B2 | 9/2003 | Terry et al. | | 2004/0034394 A1 | 2/2004 | Woods et al. |
| 6,626,839 B2 | 9/2003 | Doten et al. | | 2004/0054292 A1 | 3/2004 | Sun et al. |
| 6,666,826 B2 | 12/2003 | Salo et al. | | 2004/0062852 A1 | 4/2004 | Schroeder et al. |
| 6,668,191 B1 | 12/2003 | Boveja | | 2004/0064172 A1 | 4/2004 | McVenes et al. |
| 6,669,645 B2 | 12/2003 | Narimatsu et al. | | 2004/0102818 A1 | 5/2004 | Hakky et al. |
| 6,671,556 B2 | 12/2003 | Osorio et al. | | 2004/0186523 A1 | 9/2004 | Florio |
| 6,701,176 B1 | 3/2004 | Halperin et al. | | 2004/0193231 A1 | 9/2004 | David et al. |
| 6,701,186 B2 | 3/2004 | Spinelli et al. | | 2004/0199210 A1 | 10/2004 | Shelchuk |
| 6,704,598 B2 | 3/2004 | Ding et al. | | 2004/0210122 A1 | 10/2004 | Sieburg |
| 6,718,212 B2 | 4/2004 | Parry et al. | | 2004/0210271 A1 | 10/2004 | Campen et al. |
| 6,748,272 B2 | 6/2004 | Carlson et al. | | 2004/0215263 A1 | 10/2004 | Virag et al. |
| 6,766,189 B2 | 7/2004 | Yu et al. | | 2004/0249416 A1 | 12/2004 | Yun et al. |
| 6,768,923 B2 | 7/2004 | Ding et al. | | 2004/0249417 A1 | 12/2004 | Ransbury et al. |
| 6,779,257 B2 | 8/2004 | Kiepen et al. | | 2004/0254616 A1 | 12/2004 | Rossing et al. |
| 6,826,428 B1 | 11/2004 | Chen et al. | | 2005/0010263 A1 | 1/2005 | Schaurte |
| 6,850,801 B2 | 2/2005 | Kieval et al. | | 2005/0021092 A1 | 1/2005 | Yun et al. |
| 6,859,667 B2 | 2/2005 | Goode | | 2005/0065553 A1 | 3/2005 | Ben Ezra et al. |
| 6,876,881 B2 | 4/2005 | Baumann et al. | | 2005/0143779 A1 | 6/2005 | Libbus |
| 6,894,204 B2 | 5/2005 | Dunshee | | 2005/0143785 A1 | 6/2005 | Libbus |
| 6,907,285 B2 | 6/2005 | Denker et al. | | 2005/0149126 A1 | 7/2005 | Libbus |
| 6,922,585 B2 | 7/2005 | Zhou et al. | | 2005/0149127 A1 | 7/2005 | Libbus |
| 6,935,344 B1 | 8/2005 | Aboul-Hosn | | 2005/0149128 A1 | 7/2005 | Heil et al. |
| 6,937,896 B1 | 8/2005 | Kroll | | 2005/0149129 A1 | 7/2005 | Libbus et al. |
| 6,942,622 B1 | 9/2005 | Turcott | | 2005/0149130 A1 | 7/2005 | Libbus |
| 6,942,686 B1 | 9/2005 | Barbut et al. | | 2005/0149131 A1 | 7/2005 | Libbus et al. |
| 6,985,774 B2 | 1/2006 | Kieval et al. | | 2005/0149132 A1 | 7/2005 | Libbus |
| 7,010,337 B2 | 3/2006 | Furnary et al. | | 2005/0149133 A1 | 7/2005 | Libbus et al. |
| 7,092,755 B2 | 8/2006 | Florio | | 2005/0149143 A1 | 7/2005 | Libbus et al. |
| 7,123,961 B1 | 10/2006 | Kroll et al. | | 2005/0149155 A1 | 7/2005 | Scheiner et al. |

| | | |
|---|---|---|
| 2005/0149156 A1 | 7/2005 | Libbus et al. |
| 2005/0154418 A1 | 7/2005 | Kieval et al. |
| 2005/0182468 A1 | 8/2005 | Hunter et al. |
| 2005/0197675 A1 | 9/2005 | David et al. |
| 2005/0251212 A1 | 11/2005 | Kieval et al. |
| 2006/0004417 A1 | 1/2006 | Rossing et al. |
| 2006/0079945 A1 | 4/2006 | Libbus et al. |
| 2006/0089678 A1 | 4/2006 | Shalev |
| 2006/0100668 A1 | 5/2006 | Ben-David et al. |
| 2006/0111626 A1 | 5/2006 | Rossing et al. |
| 2006/0111745 A1 | 5/2006 | Foreman et al. |
| 2006/0206155 A1 | 9/2006 | Ben-David et al. |
| 2006/0224222 A1 | 10/2006 | Bradley et al. |
| 2007/0021790 A1 | 1/2007 | Kieval et al. |
| 2007/0021792 A1 | 1/2007 | Kieval et al. |
| 2007/0021794 A1 | 1/2007 | Kieval et al. |
| 2007/0021796 A1 | 1/2007 | Kieval et al. |
| 2007/0021797 A1 | 1/2007 | Kieval et al. |
| 2007/0021798 A1 | 1/2007 | Kieval et al. |
| 2007/0021799 A1 | 1/2007 | Kieval et al. |
| 2007/0038255 A1 | 2/2007 | Kieval et al. |
| 2007/0038260 A1 | 2/2007 | Kieval et al. |
| 2007/0038261 A1 | 2/2007 | Kieval et al. |
| 2007/0038262 A1 | 2/2007 | Kieval et al. |
| 2007/0038278 A1 | 2/2007 | Zarembo |
| 2007/0049989 A1 | 3/2007 | Rossing et al. |
| 2007/0060972 A1 | 3/2007 | Kieval et al. |
| 2007/0106340 A1 | 5/2007 | Bolea et al. |
| 2007/0161912 A1 | 7/2007 | Zhang et al. |
| 2007/0167984 A1 | 7/2007 | Kieval et al. |
| 2007/0179543 A1 | 8/2007 | Ben-David et al. |
| 2007/0185542 A1 | 8/2007 | Bolea et al. |
| 2007/0185543 A1 | 8/2007 | Rossing et al. |
| 2007/0191895 A1 | 8/2007 | Foreman et al. |
| 2007/0191904 A1 | 8/2007 | Libbus et al. |
| 2008/0049376 A1 | 2/2008 | Stevenson et al. |
| 2008/0097540 A1 | 4/2008 | Bolea et al. |
| 2008/0167694 A1 | 7/2008 | Bolea et al. |
| 2008/0167699 A1 | 7/2008 | Kieval et al. |
| 2008/0171923 A1 | 7/2008 | Bolea et al. |
| 2008/0172101 A1 | 7/2008 | Bolea et al. |
| 2008/0177339 A1 | 7/2008 | Bolea et al. |
| 2008/0177348 A1 | 7/2008 | Bolea et al. |
| 2008/0177349 A1 | 7/2008 | Kieval et al. |
| 2008/0177350 A1 | 7/2008 | Kieval et al. |
| 2008/0177364 A1 | 7/2008 | Bolea et al. |
| 2008/0177365 A1 | 7/2008 | Bolea et al. |
| 2008/0177366 A1 | 7/2008 | Bolea et al. |
| 2008/0215111 A1 | 9/2008 | Kieval et al. |
| 2009/0069738 A1 | 3/2009 | Rossing et al. |
| 2009/0228065 A1 | 9/2009 | Bolea et al. |
| 2009/0234418 A1 | 9/2009 | Kieval et al. |

FOREIGN PATENT DOCUMENTS

| | | |
|---|---|---|
| WO | WO 97/18856 | 5/1997 |
| WO | WO 98/02209 | 1/1998 |
| WO | WO 99/26530 | 6/1999 |
| WO | WO 99/42039 | 8/1999 |
| WO | WO 99/42176 | 8/1999 |
| WO | WO 99/51286 A1 | 10/1999 |
| WO | WO 00/16686 | 3/2000 |
| WO | WO 01/00273 | 1/2001 |
| WO | WO01/76469 | 10/2001 |
| WO | WO 02/26314 | 4/2002 |
| WO | WO02/26318 | 4/2002 |
| WO | WO 02/070039 | 9/2002 |
| WO | WO03/018107 | 3/2003 |
| WO | WO 03/076008 | 9/2003 |

OTHER PUBLICATIONS

Persson et al. "Effect of sino-aortic denervation in comparison to cardiopulmonary deafferentiation on long-term blood pressure in conscious dogs" Plugers Arch (1988) 411: 160-166.*

Bilgutay et al., "Baropacing, a New Concept in the Treatment of Hypertension," from *Baroreceptors and Hypertension Proceedings of an International Symposium*, (Nov. 1965), p. 425-437.

Bilgutay et al., "Surgical Treatment of Hypertension with Reference to Baropacing," *Am. J of Cardiology*, vol. 17, (May 1966), pp. 663-667.

Bock et al, "Fine Structure of Baroreceptor Terminals in the Carotid Sinus of Guinea Pigs and Mice," *Cell & Tissue Research*, vol. 170, (1976), pp. 95-112.

Brattstrom, "Influence of Continuous and Intermittent (R-Wave Triggered) Electrical Stimulation of the Carotid Sinus Nerve on the Static Characteristic of the Circularoty Regulator," *Experientia*, vol. 28, (1972), pp. 414-416.

Coleridge et al., "Impulse in Slowly Conducting Vagal Fibers from Afferent Endings in the Veins, Atria, and Arteries of Dogs and Cats," *Circ. Res.*, vol. 33, (Jul. 1973), pp. 87-97.

Correspondence, *The New England of Journal of Medicine*, vol. 281, No. 2., (Jul. 3, 1969), p. 103.

Eckberg et al., "Baroreflex anatomy" In: Monographs of the Physiological Society (43): *Human Baroreflex in Health and Disease*. Oxford, UK: Clarendon Press, (1992), pp. 19-30.

Goldberger et al., "New Technique for Vagal Nerve Stimulation," *Journal of Neuroscience Methods*, vol. 91, (1999), pp. 109-114.

Hainsworth, "Cardiovascular Reflexes From Ventricular & Coronary Receptors," *Adv. Exp. Med. Biol.*, vol. 381, (1999), pp. 157-174.

Harrison, "Carotid Sinus Stimulation for the Treatment of Angina Pectoris," *Official Journal of the Calif. Medical Assoc.*, vol. 112, No. 3, (Mar. 1970), pp. 78-79.

Itoh, "Studies on the Carotid Body & the Carotid Sinus Effects on the Heart by Electrical Stimulation of the Carotid Sinus Wall," *Jap. Heart J.*, vol. 13, No. 2, (Mar. 1972), pp. 136-149.

Kostreva et al., "Hepatic Vein, Hapatic Parenchymal, and Inferior Vena Caval Mechanoreceptors with Phrenic Afferents," *Am. J. Physiol.*, vol. 265, 1993, pp. G15-G20.

Krauhs, "Structure of Rat Aortic Baroreceptors & Their Relationship to Connective Tissue," *Journal of Neurocytology*, vol. 8, (1979), pp. 401-414.

Lindblad et al., "Circulatory Effects of Carotid Sinus Stimulation & Changes in Blood Volume Distribution in Hypertensive Man", *Acta. Physiol. Scand.*, vol. 111, (Mar. 1981), pp. 299-306.

Mifflin et al., "Rapid Resetting of Low Pressure Vegal Receptors in the Superior Vena Cava of the Rat," *Circ. Res*, vol. 51,(1982) pp. 241-249.

Neufeld, "Stimulation of the Carotid Baroreceptors Using a Radio-Frequency Method," *Israel J. Med. Sci.*, vol. 1, No. 4, (Jul. 1965), pp. 630-632.

Peters et al., "Cardiovascular response to time delays of electrocardiogram-coupled electrical stimulation of carotid sinus nerves in dogs," *Journal of the Autonomic Nervous Systems*, vol. 25, (1988), pp. 173-180.

Peters et al., "The Principle of Electrical Carotid Sinus Nerve Stimulation: A Nerve Pacemaker System for Angina Pectoris and Hypertension Therapy," *Annals of Biomedical Engineering*, vol. 8 .(1980), pp. 445-458.

Rau et al., "Psychophysiology of Arterial Baroreceptors and the Etiology of Hypertension," *Biol. Psychol.*, vol. 57, (2001), pp. 179-201.

Reich, "Implantation of a Carotid Sinus Nerve Stimulator," *AORN Journal*, (Dec. 1969.), pp. 53-56.

Richter et al., "The Course of Inhibition of Sympathetic Activity during Various Patterns of Carotid Sinus Nerve Stimulation," *Pflugers Arch.*, vol. 317, (1970), pp. 110-123.

Schauerte et al., "Transvenous parasympathetic nerve stimulation in the inferior vena cava and atrioventricular conduction," *J. Cardiovasc. Electrophysiol.*, (Jan. 2000), 1 page.

Sedin, "Responses of the Cardiovascular System to Carotid Sinus Nerve Stimulation," *Upsala J Med Sci*, Vo. 81, (1976), pp. 1-17.

Silber, "The Treatment of Heart Disease," *Heart Disease*, 2.sup.nd Edition, MacMillan Publishing Co., (1987), p. 1642.

Solti, "Baropacing of the Carotid Sinus Nerve for Treatment of Intractable Hypertension," *Zeitschrift Fur Kardiologie*, band 64, Heft 4, (1975), pp. 368-374.

Solti, "The Haemodynamic Basis of Anginal Relief Produced by Stimulation of the Carotid Sinus Nerve," *Acta Medica Academiae Scientiarum Hungaricae*, vol. 30 (1-2), (1973), pp. 61-65.

Stefanadis et al. "Non-invasive heat delivery to arterial stented segments in vivo: Effect of heat on neointimal hyperplasia (Abstr)" *J Am Coll Cardiol*, #1041-89, (Feb. 2000), p. 14A.
Tarver et al, "Clinical Experience with a Helical Bipolar Stimulating Lead," *PACE*, vol. 15, Part II, (Oct. 1992), pp. 1545-1556.
Tsakiris, "Changes in Left Ventricular End Diastolic Volume Pressure Relationship After Acute Cardiac Denervation," Abstracts of the 40th sup. Scientific Sessions, Supplement II to *Circulation*, vols. XXXV & XXXXVI, (Oct. 1967), II-253, 1 sheet.
Coleridge et al., "Reflex Effects of Stimulating Baroreceptors in the Pulmonary Artery," *J. Physciol.* (1963) 166:197-210.
Ebert et al., "Fentanyl-diazepam Anesthesia with or without N2O does not Attenuate Cardiopulmonary Baroreflex-Mediated Vasoconstrictor Responses to Controlled Hypovolemia in Humans," *Anesth Analg* (1988) 67(6): 548-554.
Warzel et. al., Effects of Carotis Sinus Nerve Stimulation at Different Times in the Respiratory and Cardiac Cycles on Variability of Heart Rate and Blood Pressure of Normotensive and Renal Hypertensive Dogs, *Journal of the Autonomic Nervous System*, (1989) 26:121-127.
Warzel et. al., "The Effect of Time of Electrical Stimulation of the Carotid Sinus on the Amount of Reduction in Arterial Pressure," *Pflugers Arch.*, (1972) 337:39-44.
Yatteau, "Laryngospasm Induced by a Carotid-Sinus-Nerve Stimulator", *N Engl J Med.*, (1971) 284(13): 709-710.
Chiou et al. "Selective Vagal Denervation of the Atria Eliminates Heart Rate Variability and Baroreflex Sensitivity While Preserving Ventricular Innervation," Circulation 1998, 98:380-368.
Dickinson, "Fainting Precipitated by Collapse-Firing of Venous Baroreceptors," The Lancet: Oct. 16, 1993, 342:970-972.
Liguori et al., Arystole and Severe Bradycardia during Epidural Anesthesia in Orthopedic Patients, Anesthesiology, Jan. 1997, 86(1):250-257.
McMahon et al., "Reflex Responses from the Main Pulmonary Artery and Bifurcation in Anaesthetised Dogs," Experimental Physiology 85(4):411-420.
Nishi et al. "Afferent Fibres From Pulmonary Arterial Baroreceptors in the Left Cardiac Sympathetic Nerve of the Cat," J. Physiol. 1974, 240: 53-66.
Express Abandonment, dated Jul. 8, 2009, U.S. Appl. No. 11/482,563, filed Jul. 7, 2006.
Express Abandonment, dated Jul. 8, 2009, U.S. Appl. No. 11/482,634, filed Jul. 7, 2006.
Express Abandonment, dated Jul. 8, 2009, U.S. Appl. No. 11/482,505, filed Jul. 7, 2006.
International Search Report for International Application No. PCT/US01/30249 dated Jan. 9, 2002.
European Search Report for European Application No. E01975479 dated Aug. 29, 2005.
Partial European Search Report for European Application No. EP09158665 dated Jul. 7, 2009.
Extended European Search Report for European Application No. EP09158665 dated Sep. 29, 2009.
International Search Report for International Application No. PCT/US05/11501 dated Aug. 24, 2006.
Supplementary European Search Report for European Application No. EP05737549 dated Jan. 26, 2010.
International Search Report for International Application No. PCT/US03/09630 dated Sep. 24, 2003.
Supplementary European Search Report for European Application No. EP03716888 dated Nov. 4, 2009.
Office Action for JP 2003-579629 dated Sep. 8, 2008.
International Search Report for International Application No. PCT/US03/09764 dated Oct. 28, 2003.
Supplementary European Search Report for European Application No. EP03716913 dated Nov. 4, 2009.
International Search Report for International Application No. PCT/US06/61256 dated Jan. 2, 2008.
Nusil, White Papers (abstract only), "Drug Delivery Market Summary," published Jun. 25, 2004, retrieved from the internet <<http://www.nusil.com/whitepapers/2004/index.aspx>>.
Silverberg et al., "Treating Obstructive Sleep Apnea Improves Essential Hypertions and Quality of Life," American Family Physician, (2002) vol. 65, No. 2.
Shahar et al., "Sleep-disordered Breathing and Cardiovascular Disease: Cross-sectional Results of the Sleep Heart Health Study," American Journal of Respiratory and Critical Care Medicine, (2001), vol. 163.
Leung et al., "State of the Art: Sleep Apnea and Cardiovascular Disease," American Journal of Respiratory and Critical Care Medicine, (2001) vol. 164.
Abstracts of the 40th Scientific Sessions, Supplement II to Circulation, vols. XXXV & XXXVI, Oct. 1967, II-253, 1 sheet.
Bolter et al. "Influence of cervical sympathetic nerve stimulation on carotid sinus baroreceptor afferents," Experientia. Nov. 15, 1980;36(11):1301-1302.
Fan et al., "Graded and dynamic reflex summation of myelinated and unmyelinated rat aortic baroreceptors," Am J Physiol Regul Integr Comp Physiol, Sep. 1999;277(3):R748-756.
U.S. Appl. No. 10/284,063.
U.S. Appl. No. 12/731,104.
U.S. Appl. No. 12/762,891.
U.S. Appl. No. 12/785,287.
U.S. Appl. No. 12/616,057.
U.S. Appl. No. 12/719,696.
Eckberg et al., "Mechanism of Prolongation of the R-R Interval with Electrical Stimulation of the Carotid Sinus Nerves in Man," Circulation Research, Journal of the American Heart Association, (1972), Dallas, Texas.
Hainsworth, "Reflexes from the Heart," Physiological Reviews, vol. 71, No. 3, (1991).
Ledsome et al., "Reflex changes in hindlimb and renal vascular resistance in response to distention of the isolated pulmonary arteries of the dog," Circulation Research, Jounal of the American Heart Association, (1977), Dallas, Texas.
Ludbrook et al., "The roles of cardiac receptor and arterial baroreceptor reflexes in control of the circulation during acute change of blood volume in the conscious rabbit," Circulation Research, Journal of the American Heart Association, (1984), Dallas, Texas.
McLeod et al., "Defining inappropriate practices in prescribing for elderly people: a national consensus panel," Canadian Medical Association, (1997).
Packer, Calcium Channel blockers in chronic heart failure. The risks of "physiologically rational" therapy, Circulation, Journal of the American Heart Association,(1990), Dallas, Texas.
Persson et al., "The influence of cardiopulmonary receptors on long-term blook pressure control and plasma rennin activity in conscious dogs," Acta Physiol Scand (1987).
Pfeffer "Blood Pressure in Heart Failure: A Love-Hate Relationship," Journal of American Cardiology, (2006).
Taylor et al., "Non-hypotensive hypovolaemia reduces ascending aortic dimensions in humans," Journal of Physiology, (1995).

* cited by examiner

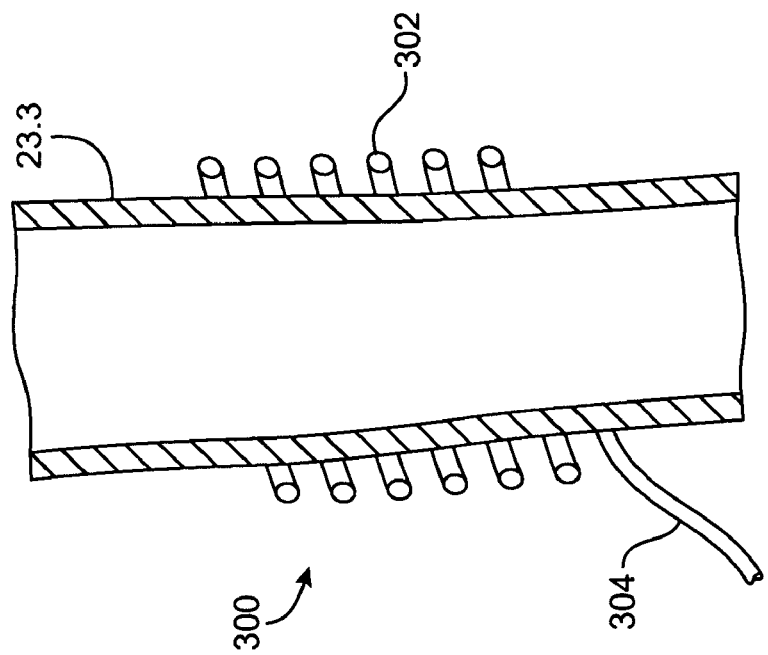
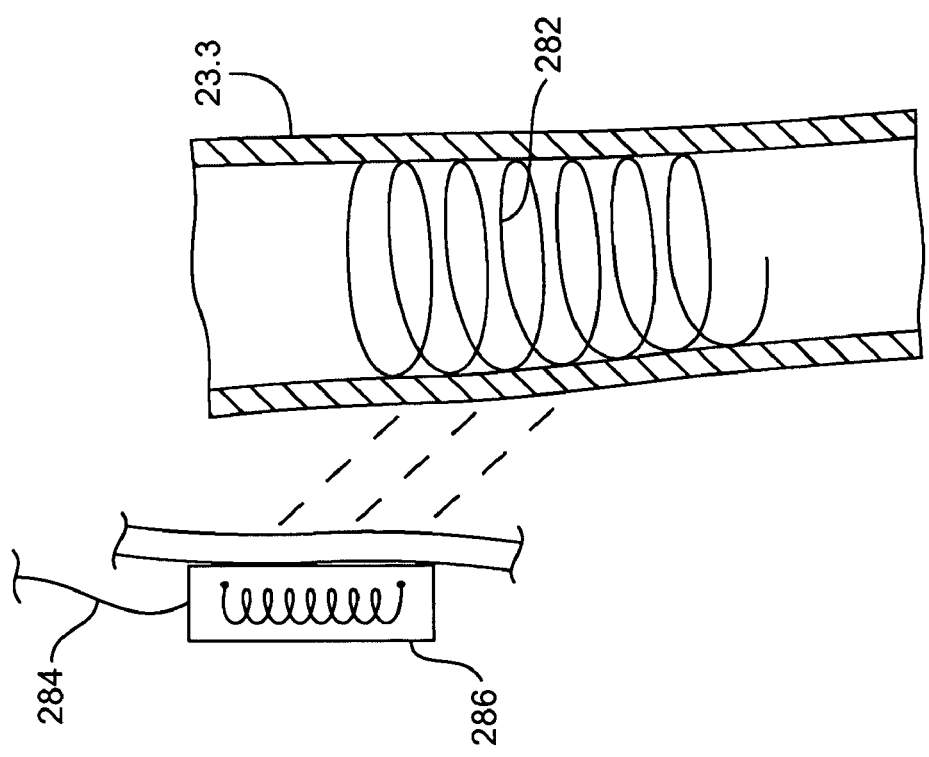

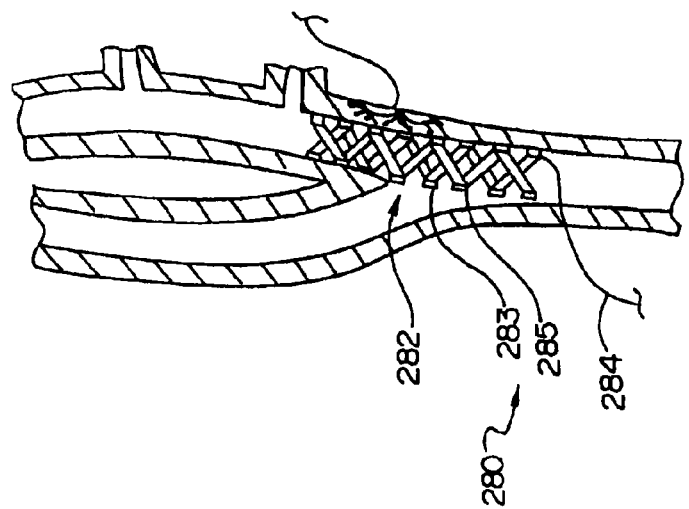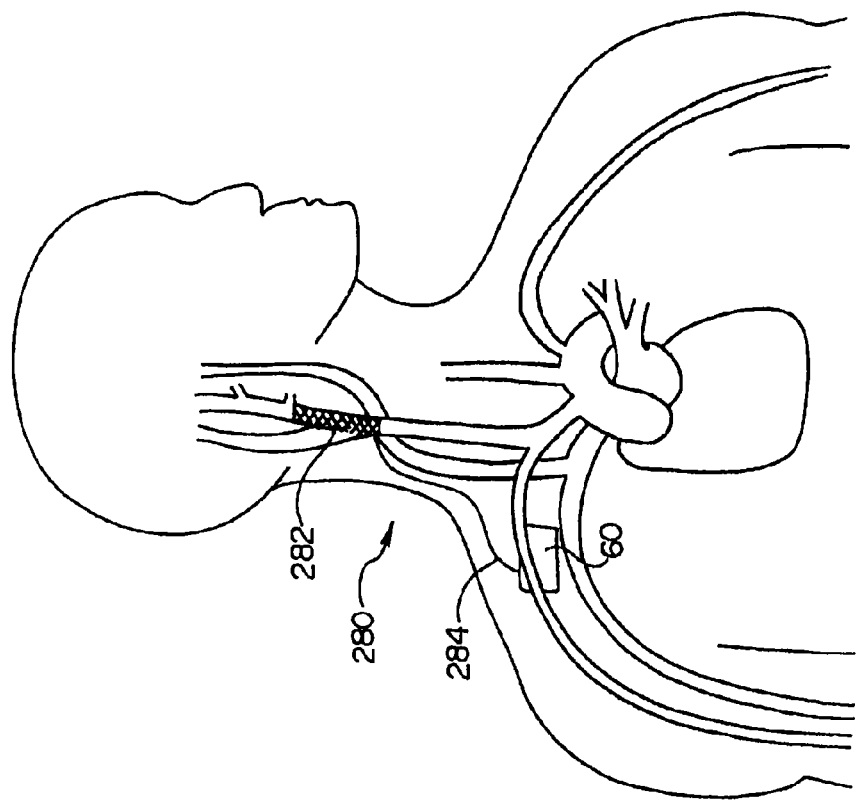

METHOD AND APPARATUS FOR STIMULATION OF BARORECEPTORS IN PULMONARY ARTERY

CROSS-REFERENCES TO RELATED APPLICATIONS

This application is a continuation of U.S. patent application Ser. No. 10/284,063, filed on Oct. 29, 2002, now issued as U.S. Pat. No. 8,086,314, the full disclosure of which is incorporated herein by reference. The parent application for this application has incorporated by reference the disclosures of the following U.S. patent applications: U.S. patent application Ser. No. 09/671,850, filed on Sep. 27, 2000, now issued as U.S. Pat. No. 6,522,926, U.S. patent application Ser. No. 09/964,079, filed on Sep. 26, 2001, now issued as U.S. Pat. No. 6,985,774, U.S. patent application Ser. No. 09/963,777, filed Sep. 26, 2001, now issued as U.S. Pat. No. 7,158,832, and U.S. patent application Ser. No. 09/963,991, filed on Sep. 26, 2001, now issued as U.S. Pat. No. 6,850,801, the disclosures of which are also effectively incorporated by reference herein.

BACKGROUND OF THE INVENTION

1. Field of the Invention

The present invention generally relates to medical devices and methods of use for the treatment and/or management of cardiovascular, renal, and neurological disorders. Specifically, the present invention relates to devices and methods for controlling the low-pressure baroreflex system for the treatment and/or management of cardiovascular, renal, and neurological disorders.

Cardiovascular disease is a major contributor to patient illness and mortality. It also is a primary driver of health care expenditure, costing more than $326 billion each year in the United States. Hypertension, or high blood pressure, is a major cardiovascular disorder that is estimated to affect over 50 million people in the United Sates alone. Hypertension occurs when the body's smaller blood vessels (arterioles) constrict, causing an increase in blood pressure. Because the blood vessels constrict, the heart must work harder to maintain blood flow at the higher pressures. Although the body may tolerate short periods of increased blood pressure, sustained hypertension may eventually result in damage to multiple body organs, including the kidneys, brain, eyes and other tissues, causing a variety of maladies associated therewith.

Heart failure is the final common expression of a variety of cardiovascular disorders, including ischemic heart disease. It is characterized by an inability of the heart to pump enough blood to meet the body's needs and results in fatigue, reduced exercise capacity and poor survival. It is estimated that approximately 5,000,000 people in the United States suffer from heart failure, directly leading to 39,000 deaths per year and contributing to another 225,000 deaths per year. Heart failure results in the activation of a number of body systems to compensate for the heart's inability to pump sufficient blood. Many of these responses are mediated by an increase in the level of activation of the sympathetic nervous system, as well as by activation of multiple other neurohormonal responses. Generally speaking, this sympathetic nervous system activation signals the heart to increase heart rate and force of contraction to increase the cardiac output; it signals the kidneys to expand the blood volume by retaining sodium and water; and it signals the arterioles to constrict to elevate the blood pressure. The cardiac, renal and vascular responses increase the workload of the heart, further accelerating myocardial damage and exacerbating the heart failure state. Accordingly, it is desirable to reduce the level of sympathetic nervous system activation in order to stop or at least minimize this vicious cycle and thereby treat or manage the heart failure.

A number of drug treatments have been proposed for the management of hypertension, heart failure and other cardiovascular disorders. These include vasodilators to reduce the blood pressure and ease the workload of the heart, diuretics to reduce fluid overload, inhibitors and blocking agents of the body's neurohormonal responses, and other medicaments. Various surgical procedures have also been proposed for these maladies. For example, heart transplantation has been proposed for patients who suffer from severe, refractory heart failure. Alternatively, an implantable medical device such as a ventricular assist device (VAD) may be implanted in the chest to increase the pumping action of the heart. Alternatively, an intra-aortic balloon pump (IABP) may be used for maintaining heart function for short periods of time, but typically no longer than one month. Other surgical procedures are available as well. No one drug, surgical procedure, or assist system, however, has provided a complete solution to the problems of hypertension and heart failure.

For these reasons, it would be desirable to provide alternative and improved methods for treating hypertension, heart failure, and other cardiovascular, neurological, and renal disorders. Such methods and systems should allow for treatment of patients where other therapies have failed or are unavailable, such as heart transplantation. It would be further desirable if the methods could lessen or eliminate the need for chronic drug use in at least some patients. Additionally, it would be desirable if the methods and systems were mechanically simple and inherently reliable, in contrast to complex mechanical systems such as VAD's, IABP's, and the like.

One particularly promising approach for improving the treatment of hypertension, heart failure, and other cardiovascular and renal disorders is described in published PCT Application No. WO 02/026314, which claims the benefit of U.S. patent application Ser. No. 09/671,850, now issued as U.S. Pat. No. 6,522,926. The full disclosures of both WO 02/026314 and U.S. Ser. No. 09/671,850, are incorporated herein by reference. WO 02/026314 describes the direct activation of baroreceptors for inducing changes in a patient's baroreflex system to control blood pressure and other patient functions. The prior applications are particularly directed at the activation of the baroreceptors present in the carotid sinus and the aortic arch. Both the carotid sinus and aortic arch are on the high-pressure or arterial side of the patient's vasculature. They are referred to as high-pressure since pressures in the systemic arterial circulation are higher than those in the veins and pulmonary circulation. Activation of the high-pressure baroreceptors can send signals to the brain that cause reflex alterations in nervous system function which result in changes in activity of target organs, including the heart, vasculature, kidneys, and the like, typically to maintain homeostasis.

While highly promising, the need to implant electrodes or other effectors on the arterial or high-pressure side of the vasculature may be disadvantageous in some respects. Arteries and other vessels on the high-pressure side of the vasculature are at risk of damage, and implantation of an electrode on or in the carotid sinus or aortic arch requires more care, and improper device implantation on the arterial side presents a small risk of arterial thromboembolism which in turn can cause stroke and other organ damage. Some arterial locations can also cause unwanted tissue or nerve stimulation due to current leakage.

Thus, it would be desirable to provide improved methods and systems for artificial and selective activation of a patient's baroreflex system in order to achieve a variety of therapeutic objectives, including the control of hypertension, renal function, heart failure, and the treatment of other cardiovascular and neurological disorders. It would be particularly desirable if such methods and systems did not require intervention on the arterial or high-pressure side of a patient's vasculature, thus lessening the risk to the patient of arterial damage and damage resulting from thromboembolism or hemorrhage. At least some of these objectives will be met by the inventions described hereinafter.

2. Description of the Background Art

U.S. Pat. Nos. 6,073,048 and 6,178,349, each having a common invention with the present application, describe the stimulation of nerves to regulate the heart, vasculature, and other body systems. Nerve stimulation for other purposes is described in, for example, U.S. Pat. Nos. 6,292,695 B1 and 5,700,282. Publications describing baropacing of the carotid arteries for controlling hypertension include Neufeld et al. (1965) *Israel J Med. Sci* 1:630-632; Bilgutay et al., Proc. Baroreceptors and Hypertension, Dayton, Ohio, Nov. 16-17, 1965, pp 425-437; Bilgutary and Lillehei (1966) *Am. J Cariol.* 17:663-667; and Itoh (1972) *Jap. Heart J* 13: 136-149. Publications which describe the existence of baroreceptors and/or related receptors in the venous vasculature and atria include Goldberger et al. (1999) *J Neuro. Meth.* 91:109-114; Kostreva and Pontus (1993) *Am. J Physiol.* 265:G15-G20; Coleridge et al. (1973) *Circ. Res.* 23:87-97; Mifflin and Kunze (1982) *Circ. Res.* 51:241-249; and Schaurte et al. (2000) *J Cardiovasc Electrophysiol.* 11:64-69.

BRIEF SUMMARY OF THE INVENTION

To address hypertension, heart failure, cardia arrhythmias, and associated cardiovascular, renal, and nervous system disorders, the present invention provides a number of devices, systems and methods by which the blood pressure, nervous system activity, and neurohormonal activity may be selectively and controllably regulated by activating baroreceptors. By selectively and controllably activating baroreceptors, the present invention reduces excessive blood pressure, sympathetic nervous system activation and neurohormonal activation, thereby minimizing their deleterious effects on the heart, vasculature and other organs and tissues.

In an exemplary embodiment, the present invention provides a system and method for treating a patient by inducing a baroreceptor signal to effect a change in the baroreflex system (e.g., reduced heart rate, reduced blood pressure, etc.). The baroreceptor signal is activated or otherwise modified by selectively activating baroreceptors. To accomplish this, the system and method of the present invention utilize a baroreceptor activation device positioned near a baroreceptor in the venous or low-pressure side of a patient's vasculature. As used hereinafter, the phrase "low-pressure side of the vasculature" will mean the venous and cardiopulmonary vasculature, including particularly the chambers in the heart, veins near the entrances to the atria, the pulmonary artery, the portal vein of the liver, the superior vena cava (SVC), the inferior vena cava (IVC), the jugular vein, the subclavian veins, the iliac veins, the femoral veins, and other peripheral areas of the vasculature where baroreceptor and baroreceptor-like receptors are found. Particular target mechanoreceptors are described in Kostreva and Pontus (1993), cited above, the full disclosure of which is incorporated herein by reference.

The baroreceptors and baroreceptor-like receptors on the low-pressure side of the vasculature will function similarly to, but not necessarily identically to, baroreceptors on the high-pressure side of the vasculature. In general, cardiovascular receptors may be sensitive to pressure and/or mechanical deformation and are referred to as baroreceptors, mechanoreceptors, pressoreceptors, stretch receptors, and the like. For cardiovascular and renal therapies, the present invention is intended to activate or otherwise interact with any or all of these types of receptors so long as such activation or interaction results in modulation of the reflex control of the patient's circulation. While there may be small structural or anatomical differences among various receptors in the vasculature, for the purposes of the present invention, activation may be directed at any of these receptors so long as they provide the desired effects. In particular, such receptors will provide afferent signals, i.e., signals to the brain, which provide the blood pressure and/or volume information to the brain which allow the brain to cause "reflex" changes in the autonomic nervous system which in turn modulate organ activity to maintain desired hemodynamics and organ perfusion. Such activation of afferent pathways may also affect brain functions in such a way that could aid in the treatment of neurologic disease.

The ability to control the baroreflex response and cardiovascular, renal, and neurological function, by intervention on the low-pressure side of the vasculature is advantageous in several respects. Intervention on the venous and cardiopulmonary side of the vasculature reduces the risk of organ damage, including stroke, from systemic arterial thromboembolism. Moreover, the devices and structures used for intervening on the venous and cardiopulmonary side of the vasculature may be less complicated since the risk they pose to venous circulation is much less than to arterial circulation. Additionally, the availability of venous and cardiopulmonary baroreceptors allows placement of electrodes and other devices which reduce the risk of unwanted tissue stimulation resulting from current leakage to closely adjacent nerves, muscles, and other tissues.

Generally speaking, the baroreceptor activation device may be activated, deactivated or otherwise modulated to activate one or more baroreceptors and induce a baroreceptor signal or a change in the baroreceptor signal to thereby effect a change in the baroreflex system. The baroreceptor activation device may be activated, deactivated, or otherwise modulated continuously, periodically, or episodically. The baroreceptor activation device may comprise a wide variety of devices which utilize mechanical, electrical, thermal, chemical, biological, or other means to activate the baroreceptor. The baroreceptor may be activated directly, or activated indirectly via the adjacent vascular tissue. The baroreceptor activation device may be positioned inside the vascular lumen (i.e., intravascularly), outside the vascular wall (i.e., extravascularly) or within the vascular wall (i.e., intramurally). The particular activation patterns may be selected to mimic those which naturally occur in the venous and cardiopulmonary vasculature, which conditions might vary from those characteristic of the arterial vasculature. In other cases, the activation patterns may be different from the natural patterns and selected to achieve an optimized barosystem response.

A control system may be used to generate a control signal which activates, deactivates or otherwise modulates the baroreceptor activation device. The control system may operate in an open-loop or a closed-loop mode. For example, in the open-loop mode, the patient and/or physician may directly or remotely interface with the control system to prescribe the control signal. In the closed-loop mode, the control signal may be responsive to feedback from a sensor, wherein the response is dictated by a preset or programmable algorithm.

To address low blood pressure and other conditions requiring blood pressure augmentation, the present invention provides a number of devices, systems and methods by which the blood pressure may be selectively and controllably regulated by inhibiting or dampening baroreceptor signals. By selectively and controllably inhibiting or dampening baroreceptor signals, the present invention reduces conditions associated with low blood pressure.

To address hypertension, heart failure, cardiac arrhythmias, and their associated cardiovascular and nervous system disorders, the present invention provides a number of devices, systems and methods by which the blood pressure, nervous system activity, and neurohormonal activity may be selectively and controllably regulated by activating baroreceptors, baroreceptor-like mechanoreceptors or pressoreceptors, or the like. By selectively and controllably activating baroreceptors, the present invention reduces excessive blood pressure, sympathetic nervous system activation and neurohormonal activation, thereby minimizing their deleterious effects on the heart, vasculature and other organs and tissues.

In an exemplary embodiment, the present invention provides a system and method for treating a patient by inducing a baroreceptor signal to effect a change in the baroreflex system (e.g., reduced heart rate, reduced blood pressure, etc.). The baroreceptor signal is activated or otherwise modified by selectively activating baroreceptors. To accomplish this, the system and method of the present invention utilize a baroreceptor activation device positioned near a baroreceptor in a vein, the pulmonary vasculature, in a heart chamber, at a veno-atrial junction, or the like.

Generally speaking, the baroreceptor activation device may be activated, deactivated or otherwise modulated to activate one or more baroreceptors and induce a baroreceptor signal or a change in the baroreceptor signal to thereby effect a change in the baroreflex system. The baroreceptor activation device may be activated, deactivated, or otherwise modulated continuously, periodically, or episodically. The baroreceptor activation device may comprise a wide variety of devices which utilize mechanical, electrical, thermal, chemical, biological, or other means to activate the baroreceptor. The baroreceptor may be activated directly, or activated indirectly via the adjacent vascular tissue. The baroreceptor activation device may be positioned inside the vascular lumen (i.e., intravascularly), outside the vascular wall (i.e., extravascularly) or within the vascular wall (i.e., intramurally).

A control system may be used to generate a control signal which activates, deactivates or otherwise modulates the baroreceptor activation device. The control system may operate in an open-loop or a closed-loop mode. For example, in the open-loop mode, the patient and/or physician may directly or remotely interface with the control system to prescribe the control signal. In the closed-loop mode, the control signal may be responsive to feedback from a sensor, wherein the response is dictated by a preset or programmable algorithm.

To address low blood pressure and other conditions requiring blood pressure augmentation, the present invention provides a number of devices, systems and methods by which the blood pressure may be selectively and controllably regulated by inhibiting or dampening baroreceptor signals. By selectively and controllably inhibiting or dampening baroreceptor signals, the present invention reduces conditions associated with low blood pressure.

BRIEF DESCRIPTION OF THE DRAWINGS

FIG. 16 is a schematic illustration of a baroreceptor activation device in the form of an internal conductive structure, activated by an external inductor, which electrically or thermally induces a baroreceptor signal in accordance with an embodiment of the present invention.

FIG. 17 is a schematic illustration of a baroreceptor activation device in the form of an external conductive structure which electrically or thermally induces a baroreceptor signal in accordance with an embodiment of the present invention.

FIGS. 23A and 23B are schematic illustrations of a baroreceptor activation device in the form of an internal bipolar conductive structure which electrically or thermally induces a baroreceptor signal in accordance with an embodiment of the present invention.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
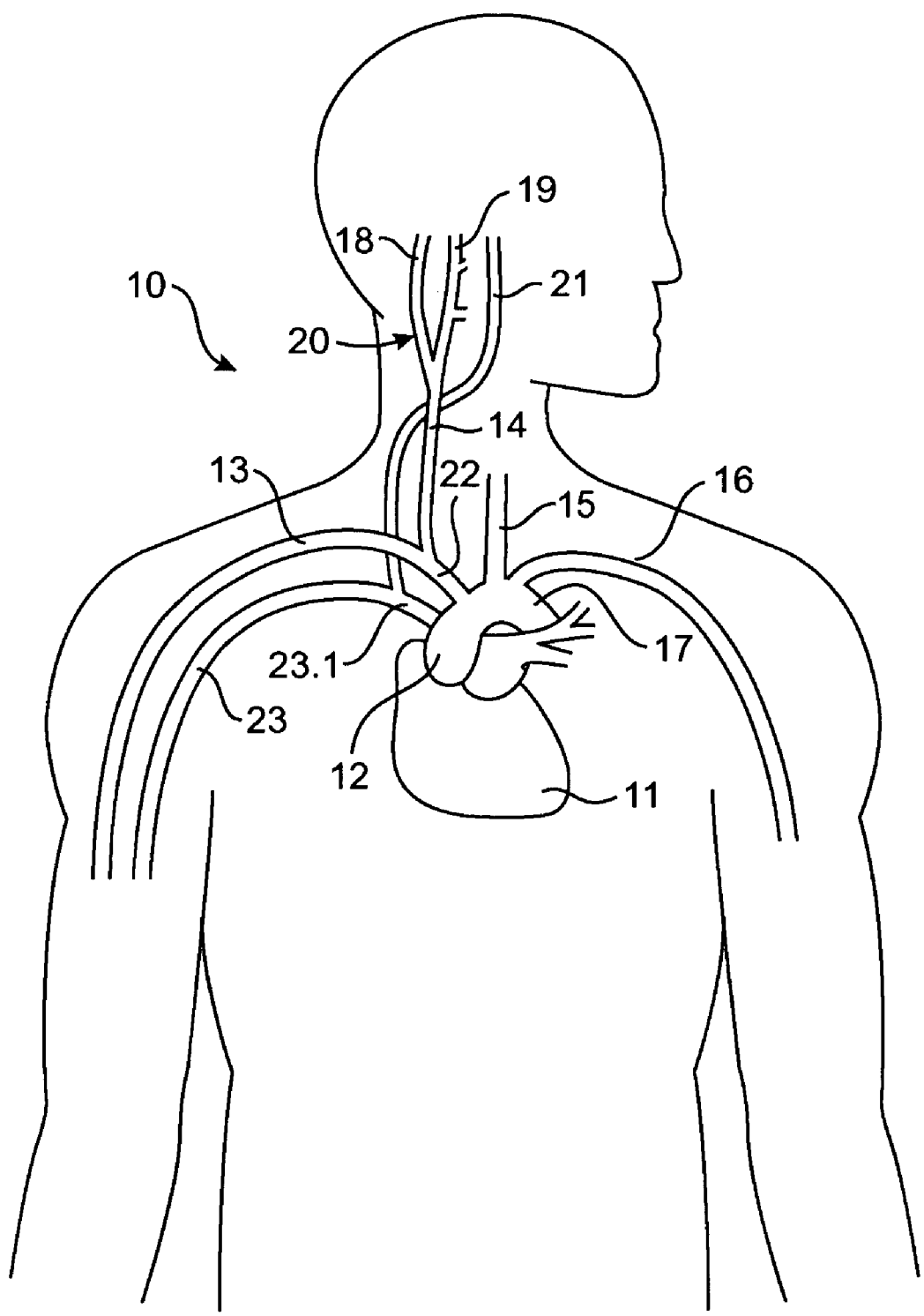
FIG. 1 is a schematic illustration of the upper torso of a human body showing the major arteries and veins and associated anatomy.

To better understand the present invention, it may be useful to explain some of the basic vascular anatomy associated with the cardiovascular system. Refer to FIG. 1 which is a schematic illustration of the upper torso of a human body 10 showing some of the major arteries and veins of the cardiovascular system. The left ventricle of the heart 11 pumps oxygenated blood up into the aortic arch 12. The right subclavian artery 13, the right common carotid artery 14, the left common carotid artery 15 and the left subclavian artery 16 branch off the aortic arch 12 proximal of the descending thoracic aorta 17. Although relatively short, a distinct vascular segment referred to as the brachiocephalic artery 22 connects the right subclavian artery 13 and the right common carotid artery 14 to the aortic arch 12. The right carotid artery 14 bifurcates into the right external carotid artery 18 and the right internal carotid artery 19 at the right carotid sinus 20. Although not shown for purposes of clarity only, the left carotid artery 15 similarly bifurcates into the left external carotid artery and the left internal carotid artery at the left carotid sinus.

From the aortic arch 12, oxygenated blood flows into the carotid arteries 18/19 and the subclavian arteries 13/16. From the carotid arteries 18/19, oxygenated blood circulates through the head and cerebral vasculature and oxygen depleted blood returns to the heart 11 by way of the jugular veins, of which only the right internal jugular vein 21 is shown for sake of clarity. From the subclavian arteries 13/16, oxygenated blood circulates through the upper peripheral vasculature and oxygen depleted blood returns to the heart by way of the subclavian veins, of which only the right subclavian vein 23 is shown, also for sake of clarity. Deoxygenated blood from the upper torso and head eventually return to the heart 11 through the superior vena cava 23.1, shown diagrammatically only. The heart 11 pumps the oxygen-depleted blood through the pulmonary system where it is re-oxygenated. The re-oxygenated blood returns to the heart 11 which pumps the re-oxygenated blood into the aortic arch as described above, and the cycle repeats. In the abdomen and lower extremities, oxygenated blood is delivered to the organs and lower limbs through the abdominal aorta 23.2. Deoxygenated blood returns to the heart through the inferior vena cava 23.3.

Within the walls of many veins, the pulmonary vasculature and the chambers of the heart, as in the walls of the carotid sinus, aorta and other arterial structures, there are baroreceptors. Baroreceptors are a type of stretch receptor used by the body to sense blood pressure and blood volume. An increase in blood pressure or volume causes the vascular wall to stretch, and a decrease in blood pressure or volume causes the vascular wall to return to its original size. In many vessels, such a cycle is repeated with each beat of the heart. In others, in particular some of the body's veins, the pressure and volume change more slowly. Because baroreceptors are located within the vascular wall, they are able to sense deformation of the adjacent tissue, which is indicative of a change in blood pressure or volume.

Figure 2:
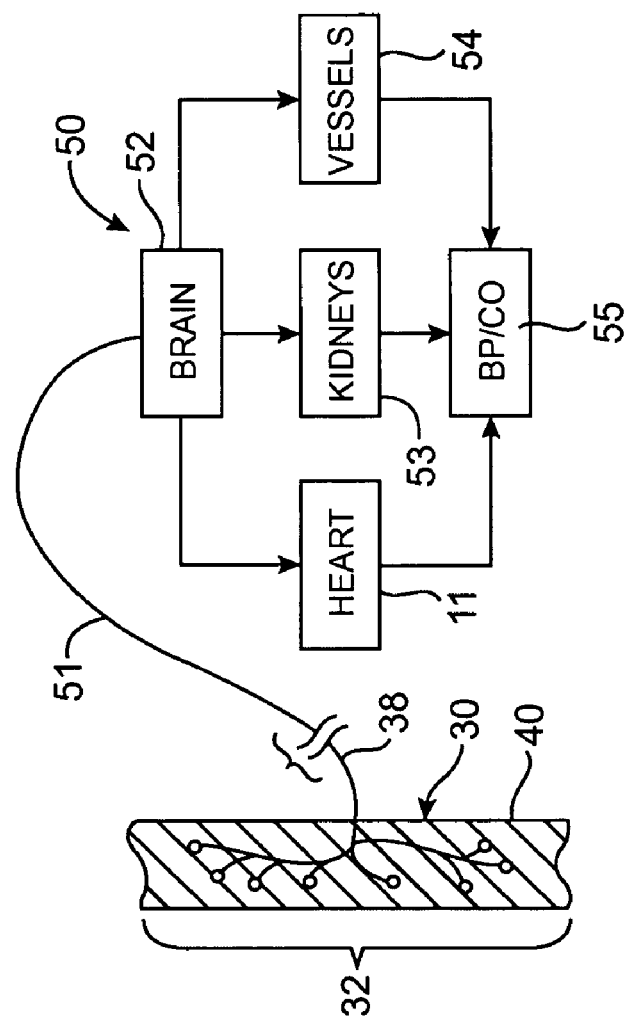
FIG. 2 is a cross-sectional schematic illustration of baroreceptors within a vascular wall.

Refer now to FIG. 2, which shows a schematic illustration of baroreceptors 30 disposed in a generic vascular wall 40 and a schematic flow chart of the baroreflex system 50. Baroreceptors 30 are profusely distributed within the arterial walls 40 of the blood vessels major arteries discussed previously, and are presently believed by the inventors to form an arbor 32 as is characteristic of the analogous receptors in the arterial system as described in U.S. Pat. No. 6,522,926, previously incorporated herein by reference. A baroreceptor arbor 32 would comprise a plurality of baroreceptors 30, each of which transmits baroreceptor signals to the brain 52 via nerve 38. The baroreceptors 30 may be so profusely distributed and arborized within the vascular wall 40 that discrete baroreceptor arbors 32 are not readily discernible. To this end, those skilled in the art will appreciate that the baroreceptors 30 shown in FIG. 2 are primarily schematic for purposes of illustration and discussion. In other regions, the baroreceptors may be so sparsely distributed that activation over a relatively greater length of the vein would be required than would be with an artery where the receptors might be more concentrated.

Baroreceptor signals in the arterial vasculature are used to activate a number of body systems which collectively may be referred to as the baroreflex system 50. For the purposes of the present invention, it will be assumed that the "receptors" in the venous and cardiopulmonary vasculature and heart chambers function analogously to the baroreceptors in the arterial vasculature, but such assumption is not intended to limit the present invention in any way. In particular, the methods described herein will function and achieve at least some of the stated therapeutic objectives regardless of the precise and actual mechanism responsible for the result. Moreover, the present invention may activate baroreceptors, mechanoreceptors, pressoreceptors, or any other venous heart, or cardiopulmonary receptors which affect the blood pressure, nervous system activity, and neurohormonal activity in a manner analogous to baroreceptors in the arterial vasculation. For convenience, all such venous receptors will be referred to collectively herein as "baroreceptors." Thus for discussion purposes, it will be assumed that baroreceptors 30 are connected to the brain 52 via the nervous system 51. Thus, the brain 52 is able to detect changes in blood pressure which are indicative of cardiac output and/or blood volume. If cardiac output and/or blood volume are insufficient to meet demand (i.e., the heart 11 is unable to pump sufficient blood), the baroreflex system 50 activates a number of body systems, including the heart 11, kidneys 53, vessels 54, and other organs/tissues. Such activation of the baroreflex system 50 generally corresponds to an increase in neurohormonal activity. Specifically, the baroreflex system 50 initiates a neurohormonal sequence that signals the heart 11 to increase heart rate and increase contraction force in order to increase cardiac output, signals the kidneys 53 to increase blood volume by retaining sodium and water, and signals the vessels 54 to constrict to elevate blood pressure. The cardiac, renal and vascular responses increase blood pressure and cardiac output 55, and thus increase the workload of the heart 11. In a patient with heart failure, this further accelerates myocardial damage and exacerbates the heart failure state.

To address the problems of hypertension, heart failure, cardiac arrhythmias, renal dysfunction, and nervous system other cardiovascular disorders, the present invention basically provides a number of devices, systems and methods by which the baroreflex system 50 is activated to reduce excessive blood pressure, autonomic nervous system activity and neurohormonal activation. In particular, the present invention provides a number of devices, systems and methods by which baroreceptors 30 may be activated, thereby indicating an increase in blood pressure and signaling the brain 52 to reduce the body's blood pressure and level of sympathetic nervous system and neurohormonal activation, and increase parasympathetic nervous system activation, thus having a beneficial effect on the cardiovascular system and other body systems.

Figure 3:
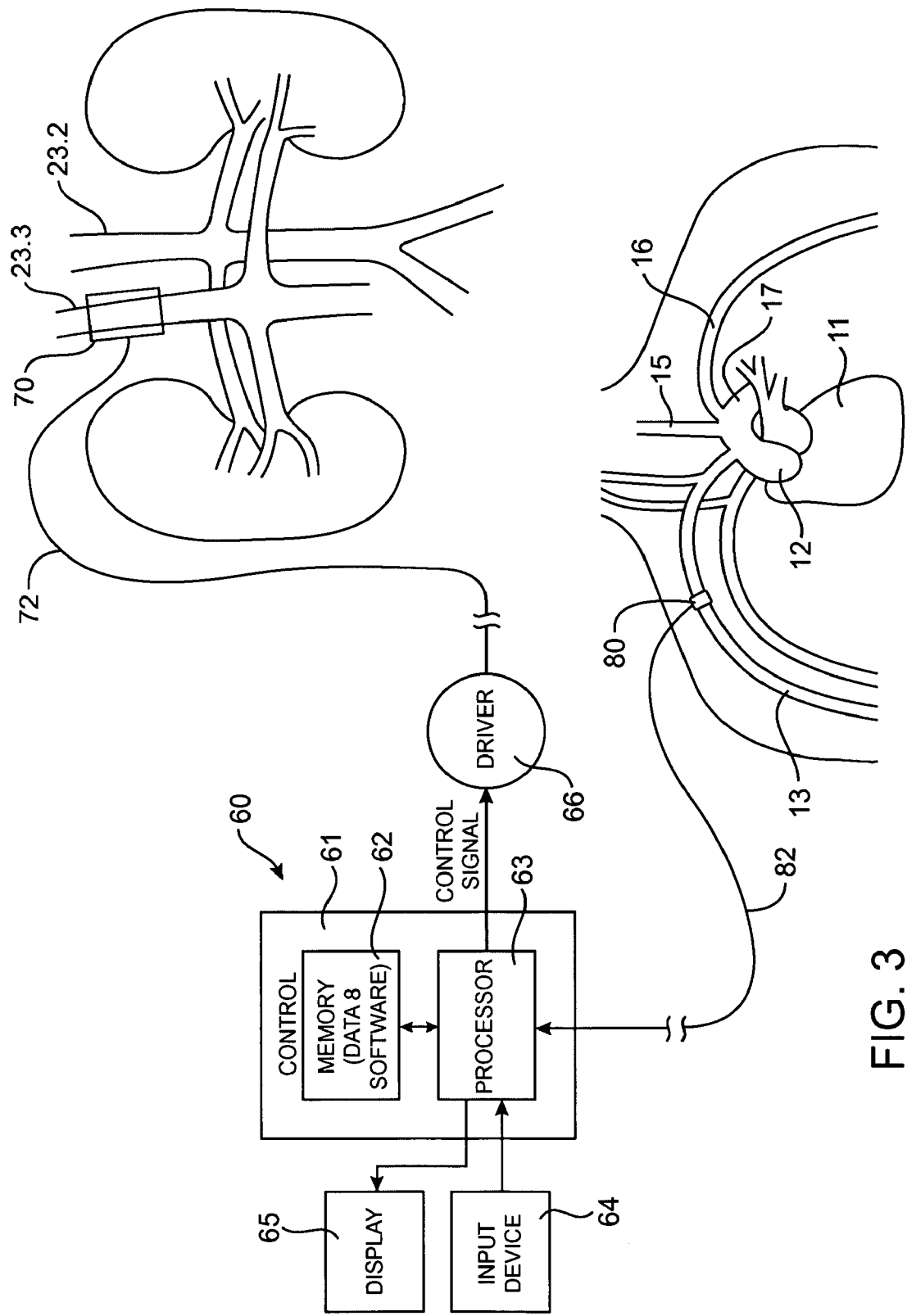
FIG. 3 is a schematic illustration of a baroreceptor activation system in accordance with the present invention.

With reference to FIG. 3, the present invention generally provides a system including a control system 60, a baroreceptor activation device 70, and a sensor 80 (optional). For purposes of illustration, the baroreceptor activation device 70 is shown to be located on, in or near the inferior vena cava 23.3, but it could also be located at the other baroreceptor target locations discussed elsewhere in this application. The exemplary control system 60, generally operates in the following manner. The sensor 80 senses and/or monitors a parameter (e.g., cardiovascular function) indicative of the need to modify the baroreflex system and generates a signal indicative of the parameter. The control system 60 generates a control signal as a function of the received sensor signal. The control signal activates, deactivates or otherwise modulates the baroreceptor activation device 70. Typically, activation of the device 70 results in activation of the baroreceptors 30 (FIG. 2). Alternatively, deactivation or modulation of the baroreceptor activation device 70 may cause or modify activation of the baroreceptors 30. The baroreceptor activation device 70 may comprise a wide variety of devices which utilize mechanical, electrical, thermal, chemical, biological, or other means to activate baroreceptors 30. Thus, when the sensor 80 detects a parameter indicative of the need to modify the baroreflex system activity (e.g., excessive blood pressure), the control system 60 generates a control signal to modulate (e.g. activate) the baroreceptor activation device 70 thereby inducing a baroreceptor 30 signal that is perceived by the brain 52 to be apparent excessive blood pressure. When the sensor 80 detects a parameter indicative of normal body function (e.g., normal blood pressure), the control system 60 generates a control signal to modulate (e.g., deactivate) the baroreceptor activation device 70.

As mentioned previously, the baroreceptor activation device 70 may comprise a wide variety of devices which utilize mechanical, electrical, thermal, chemical, biological or other means to activate the baroreceptors 30. Specific embodiments of the generic baroreceptor activation device 70 are discussed with reference to FIGS. 4-21. In most instances, particularly the mechanical activation embodiments, the baroreceptor activation device 70 indirectly activates one or more baroreceptors 30 by stretching or otherwise deforming the vascular wall 40 surrounding the baroreceptors 30. In some other instances, particularly the non-mechanical activation embodiments, the baroreceptor activation device 70 may directly activate one or more baroreceptors 30 by changing the electrical, thermal or chemical environment or potential across the baroreceptors 30. It is also possible that changing the electrical, thermal or chemical potential across the tissue surrounding the baroreceptors 30 may cause the surrounding tissue to stretch or otherwise deform, thus mechanically activating the baroreceptors 30. In other instances, particularly the biological activation embodiments, a change in the function or sensitivity of the baroreceptors 30 may be induced by changing the biological activity in the baroreceptors 30 and altering their intracellular makeup and function.

All of the specific embodiments of the baroreceptor activation device 70 are suitable for implantation, and are preferably implanted using a minimally invasive percutaneous transluminal approach and/or a minimally invasive surgical approach, depending on whether the device 70 is disposed intravascularly, extravascularly or within the vascular wall 40. The baroreceptor activation device 70 may be positioned anywhere in or proximate the venous or cardiopulmonary vasculature, and/or the heart chambers, where baroreceptors capable of modulating the baroreflex system 50 are present. The baroreceptor activation device 70 will usually be implanted such that the device 70 is positioned immediately adjacent the baroreceptors 30. Alternatively, the baroreceptor activation device 70 may be outside the body such that the device 70 is positioned a short distance from but proximate to the baroreceptors 30. Preferably, the baroreceptor activation device 70 is implanted at a location which permits selective activation of the target baroreceptor, typically being in, around, or near the target baroreceptor. For purposes of illustration only, the present invention is described with reference to baroreceptor activation device 70 positioned near the inferior vena cava 23.3.

The optional sensor 80 is operably coupled to the control system 60 by electric sensor cable or lead 82. The sensor 80 may comprise any suitable device that measures or monitors a parameter indicative of the need to modify the activity of the baroreflex system. For example, the sensor 80 may comprise a physiologic transducer or gauge that measures ECG, blood pressure (systolic, diastolic, average or pulse pressure), blood volumetric flow rate, blood flow velocity, blood pH, O2 or CO2 content, mixed venous oxygen saturation (SVO2), vasoactivity, nerve activity, tissue activity or composition. Examples of suitable transducers or gauges for the sensor 80 include ECG electrodes, a piezoelectric pressure transducer, an ultrasonic flow velocity transducer, an ultrasonic volumetric flow rate transducer, a thermodilution flow velocity transducer, a capacitive pressure transducer, a membrane pH electrode, an optical detector (SVO2) or a strain gage. Although only one sensor 80 is shown, multiple sensors 80 of the same or different type at the same or different locations may be utilized.

The sensor 80 is preferably positioned in a chamber of the heart 11, or in/on a major artery such as the aortic arch 12, a common carotid artery 14/15, a subclavian artery 13/16 or the brachiocephalic artery 22, or in any of the low-pressure venous or cardiopulmonary sites, such that the parameter of interest may be readily ascertained. The sensor 80 may be disposed inside the body such as in or on an artery, a vein or a nerve (e.g. vagus nerve), or disposed outside the body, depending on the type of transducer or gauge utilized. The sensor 80 may be separate from the baroreceptor activation device 70 or combined therewith. For purposes of illustration only, the sensor 80 is shown positioned on the right subclavian artery 13.

By way of example, the control system 60 includes a control block 61 comprising a processor 63 and a memory 62. Control system 60 is connected to the sensor 80 by way of sensor cable 82. Control system 60 is also connected to the baroreceptor activation device 70 by way of electric control cable 72. Thus, the control system 60 receives a sensor signal from the sensor 80 by way of sensor cable 82, and transmits a control signal to the baroreceptor activation device 70 by way of control cable 72.

The memory 62 may contain data related to the sensor signal, the control signal, and/or values and commands provided by the input device 64. The memory 62 may also include software containing one or more algorithms defining one or more functions or relationships between the control signal and the sensor signal. The algorithm may dictate activation or deactivation control signals depending on the sensor signal or a mathematical derivative thereof. The algorithm may dictate an activation or deactivation control signal when the sensor signal falls below a lower predetermined threshold value, rises above an upper predetermined threshold value or when the sensor signal indicates a specific physiologic event.

As mentioned previously, the baroreceptor activation device 70 may activate baroreceptors 30 mechanically, electrically, thermally, chemically, biologically or otherwise. In some instances, the control system 60 includes a driver 66 to provide the desired power mode for the baroreceptor activation device 70. For example if the baroreceptor activation device 70 utilizes pneumatic or hydraulic actuation, the driver 66 may comprise a pressure/vacuum source and the cable 72 may comprise fluid line(s). If the baroreceptor activation device 70 utilizes electrical or thermal actuation, the driver 66 may comprise a power amplifier or the like and the cable 72 may comprise electrical lead(s). If the baroreceptor activation device 70 utilizes chemical or biological actuation, the driver 66 may comprise a fluid reservoir and a pressure/vacuum source, and the cable 72 may comprise fluid line(s). In other instances, the driver 66 may not be necessary, particularly if the processor 63 generates a sufficiently strong electrical signal for low level electrical or thermal actuation of the baroreceptor activation device 70.

The control system 60 may operate as a closed loop utilizing feedback from the sensor 80, or as an open loop utilizing commands received by input device 64. The open loop operation of the control system 60 preferably utilizes some feedback from the transducer 80, but may also operate without feedback. Commands received by the input device 64 may directly influence the control signal or may alter the software and related algorithms contained in memory 62. The patient and/or treating physician may provide commands to input device 64. Display 65 may be used to view the sensor signal, control signal and/or the software/data contained in memory 62.

The control signal generated by the control system 60 may be continuous, periodic, episodic or a combination thereof, as dictated by an algorithm contained in memory 62. Continuous control signals include a constant pulse, a constant train of pulses, a triggered pulse and a triggered train of pulses. Examples of periodic control signals include each of the continuous control signals described above which have a designated start time (e.g., beginning of each minute, hour or day) and a designated duration (e.g., 1 second, 1 minute, 1 hour). Examples of episodic control signals include each of the continuous control signals described above which are triggered by an episode (e.g., activation by the patient/physician, an increase in blood pressure above a certain threshold, etc.).

The control system 60 may be implanted in whole or in part. For example, the entire control system 60 may be carried externally by the patient utilizing transdermal connections to the sensor lead 82 and the control lead 72. Alternatively, the control block 61 and driver 66 may be implanted with the input device 64 and display 65 carried externally by the patient utilizing transdermal connections therebetween. As a further alternative, the transdermal connections may be replaced by cooperating transmitters/receivers to remotely communicate between components of the control system 60 and/or the sensor 80 and baroreceptor activation device 70.

Figure 1A:
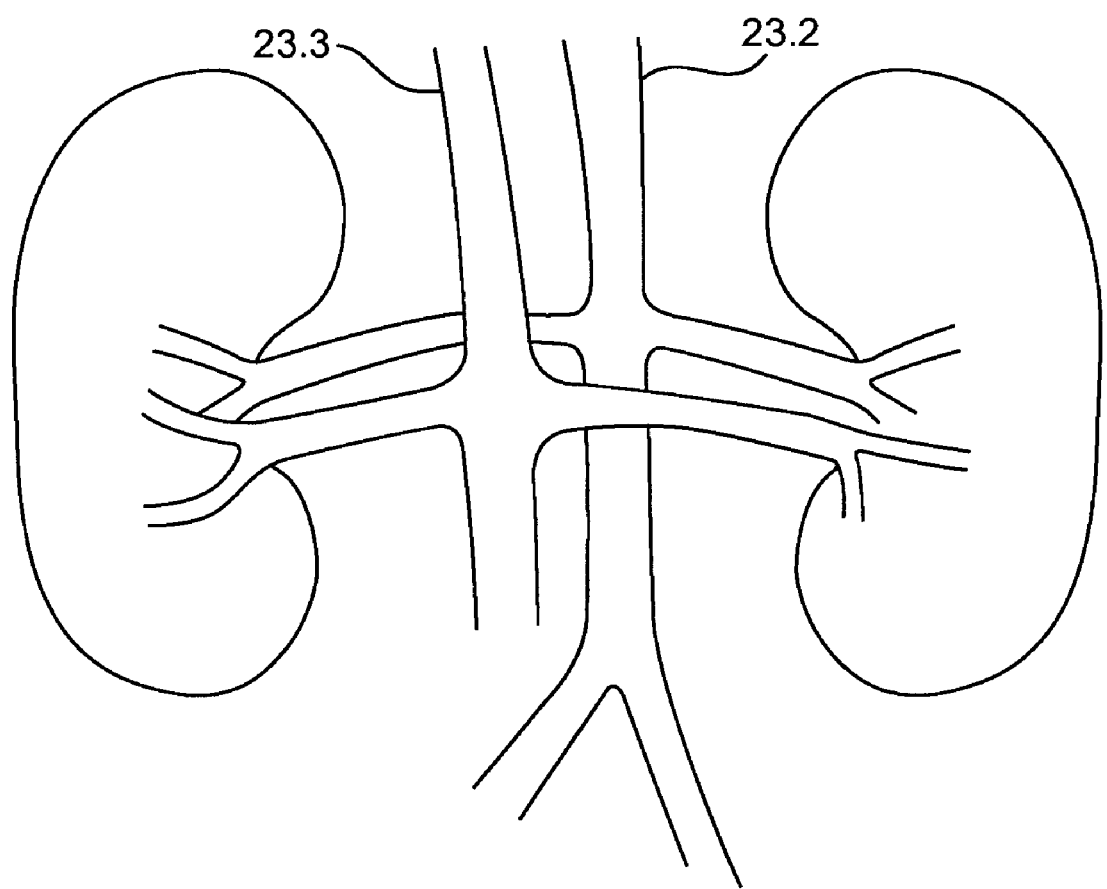
FIG. 1A is a schematic illustration of the lower abdominal vasculature including the abdominal aorta and the inferior vena cava.

With general reference to FIGS. 4-21, schematic illustrations of specific embodiments of the baroreceptor activation device 70 are shown. The design, function and use of these specific embodiments, in addition to the control system 60 and sensor 80 (not shown), are the same as described with reference to FIG. 3, unless otherwise noted or apparent from the description. In addition, the anatomical features illustrated in FIGS. 4-20 are the same as discussed with reference to FIGS. 1, 1A, and 2, unless otherwise noted. In each embodiment, the connections between the components 60/70/80 may be physical (e.g., wires, tubes, cables, etc.) or remote (e.g., transmitter/receiver, inductive, magnetic, etc.). For physical connections, the connection may travel intraarterially, intravenously, subcutaneously, or through other natural tissue paths.

Figure 4:
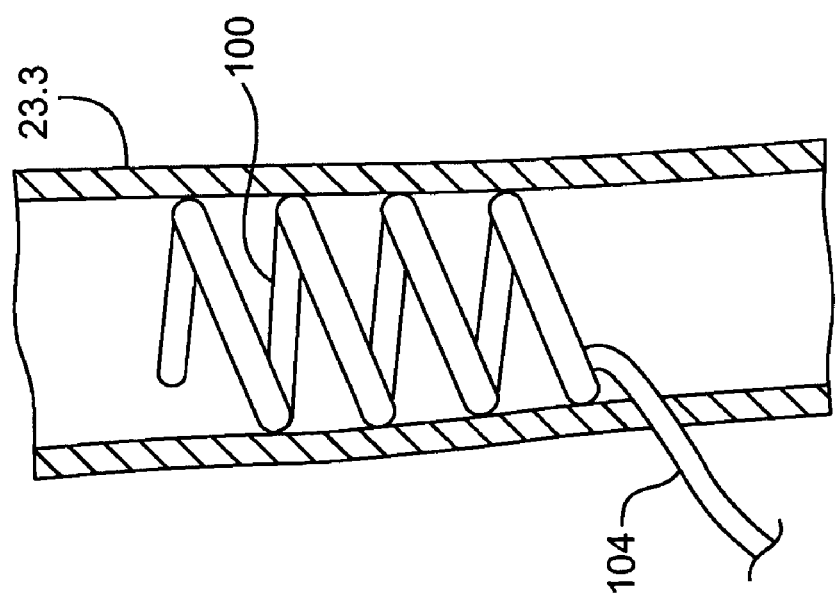
FIG. 4 is a schematic illustration of a baroreceptor activation device in the form of an internal inflatable balloon which mechanically induces a baroreceptor signal in accordance with an embodiment of the present invention.

Refer now to FIG. 4 which shows schematic illustrations of a baroreceptor activation device 100 in the form of an intravascular inflatable balloon 100. The inflatable balloon device 100 includes a helical balloon 102 which is connected to a fluid line 104. An example of a similar helical balloon is disclosed in U.S. Pat. No. 5,181,911 to Shturman, the entire disclosure of which is hereby incorporated by reference. The balloon 102 preferably has a helical geometry or any other geometry which allows blood perfusion therethrough. The fluid line 104 is connected to the driver 66 of the control system 60 (FIG. 3). In this embodiment, the driver 66 comprises a pressure/vacuum source (i.e., an inflation device) which selectively inflates and deflates the helical balloon 102. Upon inflation, the helical balloon 102 expands, preferably increasing in outside diameter only, to mechanically activate baroreceptors 30 by stretching or otherwise deforming them and/or the vascular wall 40. Upon deflation, the helical balloon 102 returns to its relaxed geometry such that the vascular wall 40 returns to its nominal state. Thus, by selectively inflating the helical balloon 102, the baroreceptors 30 adjacent thereto may be selectively activated.

As an alternative to pneumatic or hydraulic expansion utilizing a balloon, a mechanical expansion device (not shown) may be used to expand or dilate the vascular wall 40 and thereby mechanically activate the baroreceptors 30. For example, the mechanical expansion device may comprise a tubular wire braid structure that diametrically expands when longitudinally compressed as disclosed in U.S. Pat. No. 5,222,971 to Willard et al., the entire disclosure of which is hereby incorporated by reference. The tubular braid may be disposed intravascularly and permits blood perfusion through the wire mesh. In this embodiment, the driver 66 may comprise a linear actuator connected by actuation cables to opposite ends of the braid. When the opposite ends of the tubular braid are brought closer together by actuation of the cables, the diameter of the braid increases to expand the vascular wall 40 and activate the baroreceptors 30.

Figure 5:
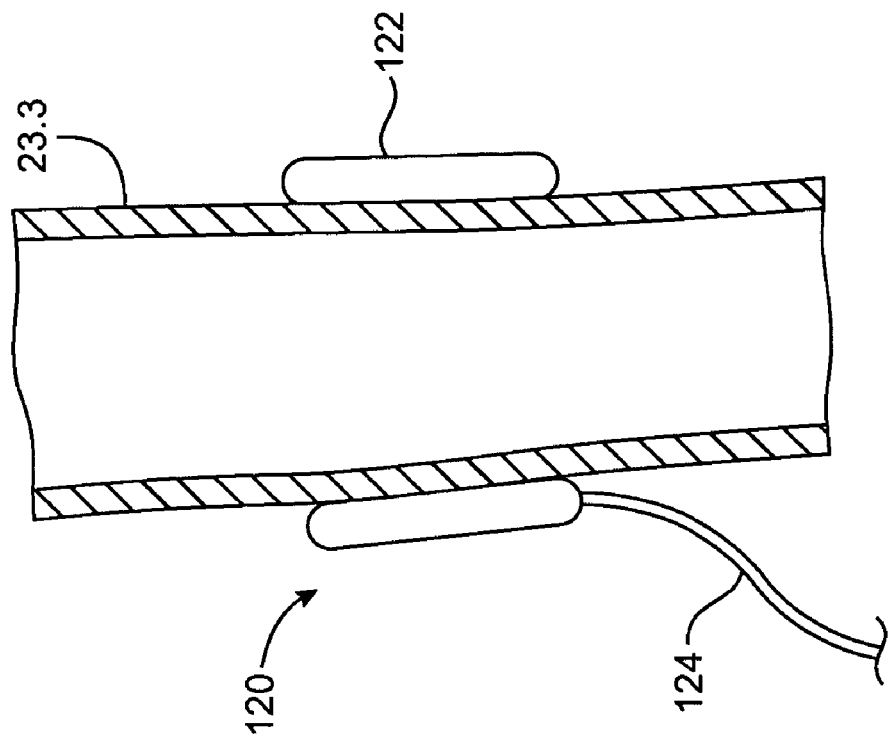
FIG. 5 is a schematic illustration of a baroreceptor activation device in the form of an external pressure cuff which mechanically induces a baroreceptor signal in accordance with an embodiment of the present invention.

Refer now to FIG. 5 which shows a baroreceptor activation device 120 in the form of an extravascular pressure cuff 120. The pressure cuff device 120 includes an inflatable cuff 122 which is connected to a fluid line 124. Examples of a similar cuffs 122 are disclosed in U.S. Pat. No. 4,256,094 to Kapp et al. and U.S. Pat. No. 4,881,939 to Newman, the entire disclosures of which are hereby incorporated by reference. The fluid line 124 is connected to the driver 66 (FIG. 3) of the control system 60. In this embodiment, the driver 66 comprises a pressure/vacuum source (i.e., an inflation device) which selectively inflates and deflates the cuff 122. Upon inflation, the cuff 122 expands, preferably increasing in inside diameter only, to mechanically activate baroreceptors 30 by stretching or otherwise deforming them and/or the vascular wall 40. Upon deflation, the cuff 122 returns to its relaxed geometry such that the vascular wall 40 returns to its nominal state. Thus, by selectively inflating the inflatable cuff 122, the baroreceptors 30 adjacent thereto may be selectively activated.

The driver 66 may be automatically actuated by the control system 60 as discussed above, or may be manually actuated. An example of an externally manually actuated pressure/vacuum source is disclosed in U.S. Pat. No. 4,709,690 to Haber, the entire disclosure of which is hereby incorporated by reference. Examples of transdermally manually actuated pressure/vacuum sources are disclosed in U.S. Pat. No. 4,586,501 to Claracq, U.S. Pat. No. 4,828,544 to Lane et al., and U.S. Pat. No. 5,634,878 to Grundei et al., the entire disclosures of which are hereby incorporated by reference.

Those skilled in the art will recognize that other external compression devices may be used in place of the inflatable cuff device 120. For example, a piston actuated by a solenoid may apply compression to the vascular wall. An example of a solenoid actuated piston device is disclosed in U.S. Pat. No. 4,014,318 to Dokum et al, and an example of a hydraulically or pneumatically actuated piston device is disclosed in U.S. Pat. No. 4,586,501 to Claracq, the entire disclosures of which are hereby incorporated by reference. Other examples include a rotary ring compression device as disclosed in U.S. Pat. No. 4,551,862 to Haber, and an electromagnetically actuated compression ring device as disclosed in U.S. Pat. No. 5,509,888 to Miller, the entire disclosures of which are hereby incorporated by reference.

Figures 6B, 6C:
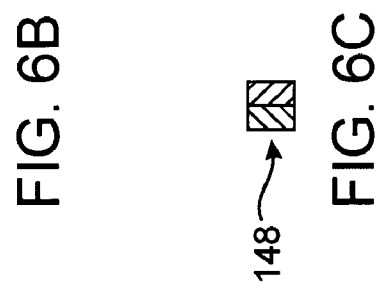
FIGS. 6B and 6C are cross-sectional views of alternative embodiments of the coil member illustrated in FIG. 6.
Figure 6A:
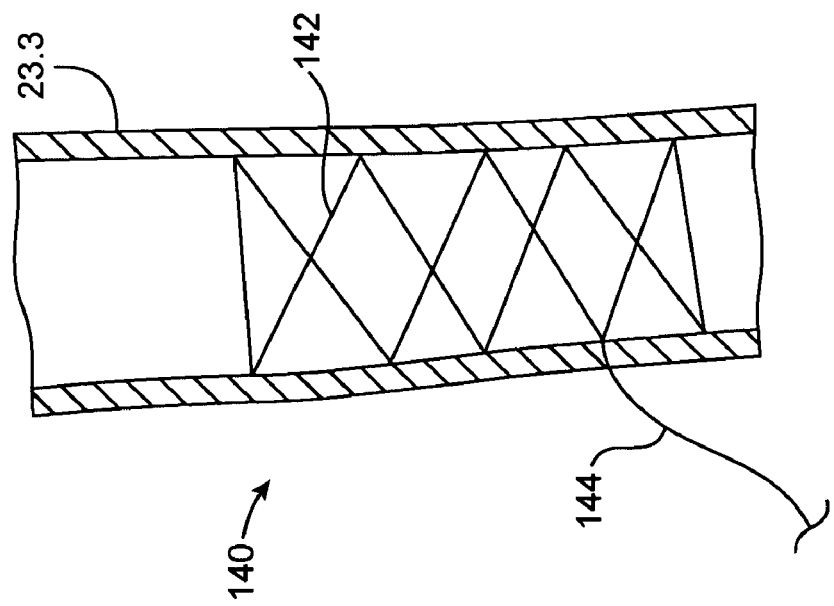
FIG. 6A is a schematic illustration of a baroreceptor activation device in the form of an internal deformable coil structure which mechanically induces a baroreceptor signal in accordance with an embodiment of the present invention.

Refer now to FIG. 6 which shows a baroreceptor activation device 140 in the form of an intravascular deformable structure. The deformable structure device 140 includes a coil, braid or other stent-like structure 142 disposed in the vascular lumen. The deformable structure 142 includes one or more individual structural members connected to an electrical lead 144. Each of the structural members forming deformable structure 142 may comprise a shape memory material 146 (e.g., nickel titanium alloy) as illustrated in FIG. 6B, or a bimetallic material 148 as illustrated in FIG. 6C. The electrical lead 144 is connected to the driver 66 of the control system 60. In this embodiment, the driver 66 comprises an electric power generator or amplifier which selectively delivers electric current to the structure 142 which resistively heats the structural members 146/148. The structure 142 may be unipolar as shown using the surrounding tissue as ground, or bipolar or multipolar using leads connected to either end of the stricture 142. Electrical power may also be delivered to the structure 142 inductively as described hereinafter with reference to FIGS. 14-16.

Upon application of electrical current to the shape memory material 146, it is resistively heated causing a phase change and a corresponding change in shape. Upon application of electrical current to the bimetallic material 148, it is resistively heated causing a differential in thermal expansion and a corresponding change in shape. In either case, the material 146/148 is designed such that the change in shape causes expansion of the structure 142 to mechanically activate baroreceptors 30 by stretching or otherwise deforming them and/or the vascular wall 40. Upon removal of the electrical current, the material 146/148 cools and the structure 142 returns to its relaxed geometry such that the baroreceptors 30 and/or the vascular wall 40 return to their nominal state. Thus, by selectively expanding the structure 142, the baroreceptors 30 adjacent thereto may be selectively activated.

Figure 7:
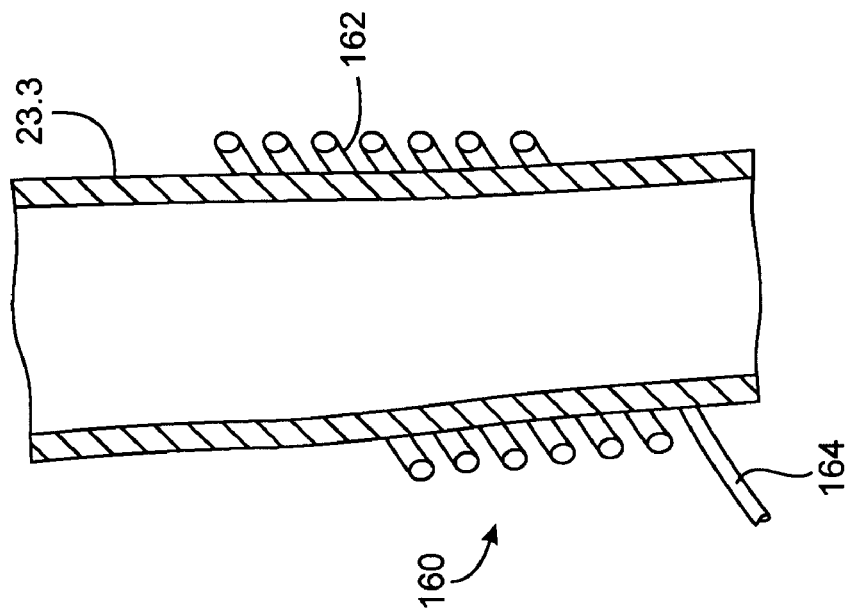
FIG. 7 is a schematic illustration of a baroreceptor activation device in the form of an external deformable coil structure which mechanically induces a baroreceptor signal in accordance with an embodiment of the present invention.

Refer now to FIG. 7 which shows a baroreceptor activation device 160 in the form of an extravascular deformable structure. The extravascular deformable structure device 160 is substantially the same as the intravascular deformable structure device 140 described with reference to FIGS. 6A and 6B, except that the extravascular device 160 is disposed about the vascular wall, and therefore compresses, rather than expands, the vascular wall 40. The deformable structure device 160 includes a coil, braid or other stent-like structure 162 comprising one or more individual structural members connected to an electrical lead 164. Each of the structural members may comprise a shape memory material 166 (e.g., nickel titanium alloy) as illustrated in FIG. 7C, or a bimetallic material 168. The structure 162 may be unipolar as shown using the surrounding tissue as ground, or bipolar or multipolar using leads connected to either end of the structure 162. Electrical power may also be delivered to the structure 162 inductively as described hereinafter with reference to FIGS. 14-16.

Upon application of electrical current to the shape memory material 166, it is resistively heated causing a phase change and a corresponding change in shape. Upon application of electrical current to the bimetallic material 168, it is resistively heated causing a differential in thermal expansion and a corresponding change in shape. In either case, the material 166/168 is designed such that the change in shape causes constriction of the structure 162 to mechanically activate baroreceptors 30 by compressing or otherwise deforming the baroreceptors 30 and/or the vascular wall 40. Upon removal of the electrical current, the material 166/168 cools and the structure 162 returns to its relaxed geometry such that the baroreceptors 30 and/or the vascular wall 40 return to their nominal state. Thus, by selectively compressing the structure 162, the baroreceptors 30 adjacent thereto may be selectively activated.

Figure 8:
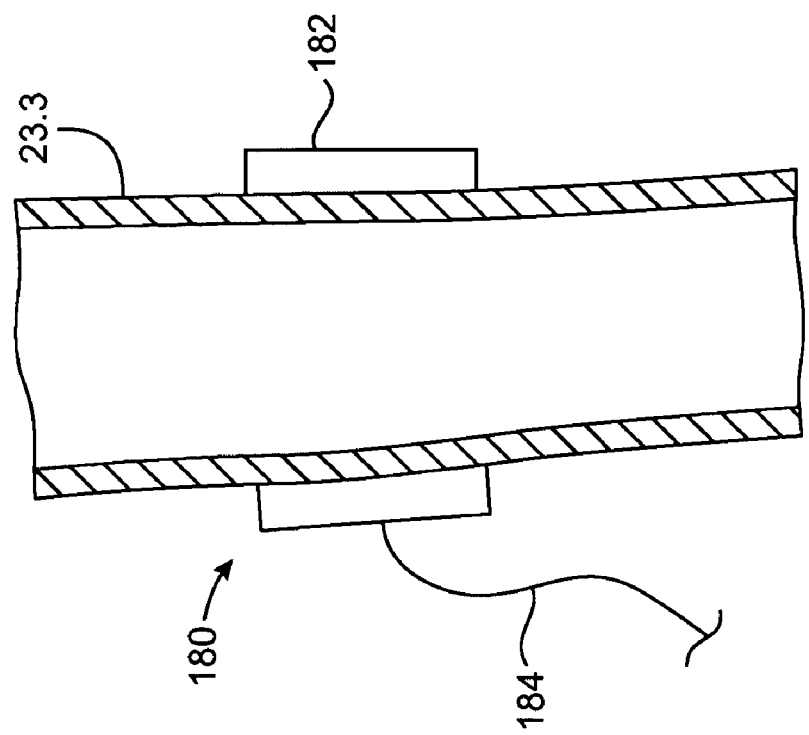
FIG. 8 is a schematic illustration of a baroreceptor activation device in the form of an external flow regulator which artificially creates back pressure to induce a baroreceptor signal in accordance with an embodiment of the present invention.

Refer now to FIG. 8 which shows a baroreceptor activation device 180 in the form of an extravascular flow regulator which artificially creates back pressure adjacent the baroreceptors 30. The flow regulator device 180 includes an external compression device 182, which may comprise any of the external compression devices described with reference to FIG. 5. The external compression device 182 is operably connected to the driver 66 of the control system 60 by way of cable 184, which may comprise a fluid line or electrical lead, depending on the type of external compression device 182 utilized. The external compression device 182 is disposed about the vascular wall distal of the baroreceptors 30. For example, the external compression device 182 may be located in the distal portions of the inferior vena cava 23.3 to create back pressure adjacent the baroreceptors 30 upstream in the inferior vena cava.

Upon actuation of the external compression device 182, the vascular wall is constricted thereby reducing the size of the vascular lumen therein. By reducing the size of the vascular lumen, pressure proximal of the external compression device 182 is increased thereby expanding the vascular wall. Thus, by selectively activating the external compression device 182 to constrict the vascular lumen and create back pressure, the baroreceptors 30 may be selectively activated.

Figure 9:
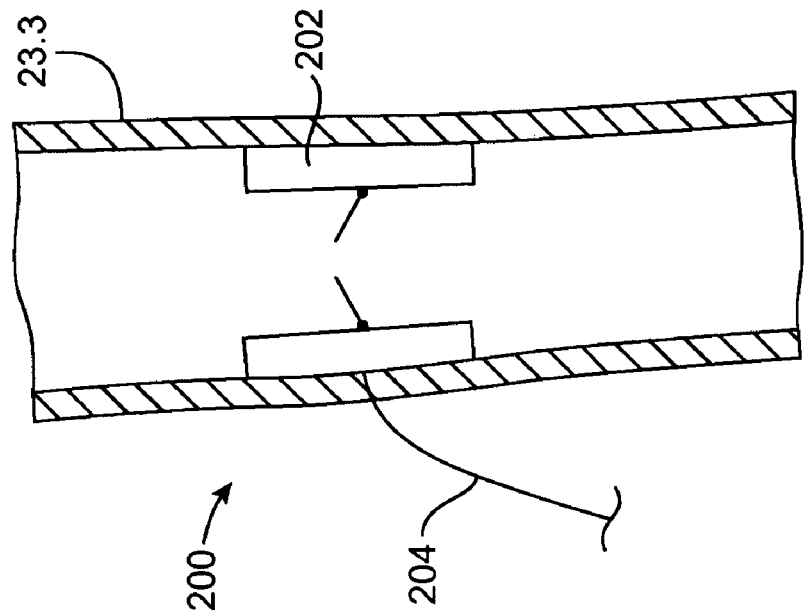
FIG. 9 is a schematic illustration of a baroreceptor activation device in the form of an internal flow regulator which artificially creates back pressure to induce a baroreceptor signal in accordance with an embodiment of the present invention.

Refer now to FIG. 9 which shows a baroreceptor activation device 200 in the form of an intravascular flow regular which artificially creates back pressure adjacent the baroreceptors 30. The intravascular flow regulator device 200 is substantially similar in function and use as extravascular flow regulator 180 described with reference to FIG. 8, except that the intravascular flow regulator device 200 is disposed in the vascular lumen.

Intravascular flow regulator 200 includes an internal valve 202 to at least partially close the vascular lumen distal of the baroreceptors 30. By at least partially closing the vascular lumen distal of the baroreceptors 30, back pressure is created proximal of the internal valve 202 such that the vascular wall expands to activate the baroreceptors 30. The internal valve 202 may be positioned at any of the locations described with reference to the external compression device 182, except that the internal valve 202 is placed within the vascular lumen. Specifically, the internal compression device 202 may be located in the distal portions of the vasculature to create back pressure adjacent to the baroreceptors 30 in the veins or cardiopulmonary system.

The internal valve 202 is operably coupled to the driver 66 of the control system 60 by way of electrical lead 204. The control system 60 may selectively open, close or change the flow resistance of the valve 202 as described in more detail hereinafter. The internal valve 202 may include valve leaflets 206 (bi-leaflet or tri-leaflet) which rotate inside housing 208 about an axis between an open position and a closed position. The closed position may be completely closed or partially closed, depending on the desired amount of back pressure to be created. The opening and closing of the internal valve 202 may be selectively controlled by altering the resistance of leaflet 206 rotation or by altering the opening force of the leaflets 206. The resistance of rotation of the leaflets 206 may be altered utilizing electromagnetically actuated metallic bearings carried by the housing 208. The opening force of the leaflets 206 may be altered by utilizing electromagnetic coils in each of the leaflets to selectively magnetize the leaflets such that they either repel or attract each other, thereby facilitating valve opening and closing, respectively.

A wide variety of intravascular flow regulators may be used in place of internal valve 202. For example, internal inflatable balloon devices as disclosed in U.S. Pat. No. 4,682,583 to Burton et al. and U.S. Pat. No. 5,634,878 to Grundei et al., the entire disclosures of which is hereby incorporated by reference, may be adapted for use in place of valve 202. Such inflatable balloon devices may be operated in a similar manner as the inflatable cuff 122 described with reference to FIG. 5. Specifically, in this embodiment, the driver 66 would comprises a pressure/vacuum source (i.e., an inflation device) which selectively inflates and deflates the internal balloon. Upon inflation, the balloon expands to partially occlude blood flow and create back pressure to mechanically activate baroreceptors 30 by stretching or otherwise deforming them and/or the vascular wall 40. Upon deflation, the internal balloon returns to its normal profile such that flow is not hindered and back pressure is eliminated. Thus, by selectively inflating the internal balloon, the baroreceptors 30 proximal thereof may be selectively activated by creating back pressure.

Figure 10:
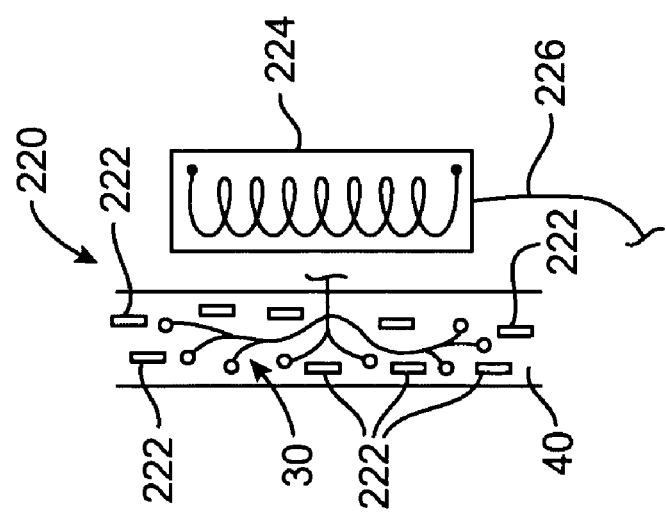
FIG. 10 is a schematic illustration of a baroreceptor activation device in the form of a magnetic device which mechanically induces a baroreceptor signal in accordance with an embodiment of the present invention.

Refer now to FIG. 10 which shows a baroreceptor activation device 220 in the form of magnetic particles 222 disposed in the vascular wall 40. The magnetic particles 222 may comprise magnetically responsive materials (i.e., ferrous based materials) and may be magnetically neutral or magnetically active. Preferably, the magnetic particles 222 comprise permanent magnets having an elongate cylinder shape with north and south poles to strongly respond to magnetic fields. The magnetic particles 222 are actuated by an electromagnetic coil 224 which is operably coupled to the driver 66 of the control system 60 by way of an electrical cable 226. The electromagnetic coil 224 may be implanted as shown, or located outside the body, in which case the driver 66 and the remainder of the control system 60 would also be located outside the body. By selectively activating the electromagnetic coil 224 to create a magnetic field, the magnetic particles 222 may be repelled, attracted or rotated. Alternatively, the magnetic field created by the electromagnetic coil 224 may be alternated such that the magnetic particles 222 vibrate within the vascular wall 40. When the magnetic particles are repelled, attracted, rotated, vibrated or otherwise moved by the magnetic field created by the electromagnetic coil 224, the baroreceptors 30 are mechanically activated.

The electromagnetic coil 224 is preferably placed as close as possible to the magnetic particles 222 in the vascular wall 40, and may be placed intravascularly, extravascularly, or in any of the alternative locations discussed with reference to inductor shown in FIGS. 14-16. The magnetic particles 222 may be implanted in the vascular wall 40 by injecting a ferro-fluid or a ferro-particle suspension into the vascular wall adjacent to the baroreceptors 30. To increase biocompatibility, the particles 222 may be coated with a ceramic, polymeric or other inert material. Injection of the fluid carrying the magnetic particles 222 is preferably performed percutaneously.

Figure 11:
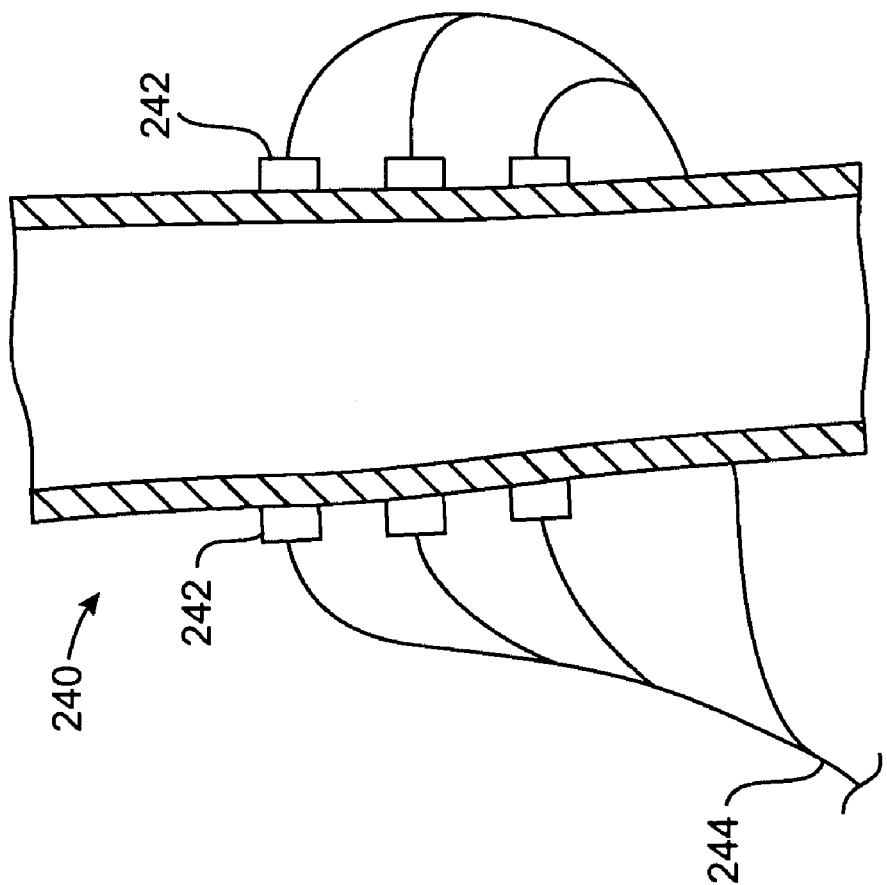
FIG. 11 is a schematic illustration of a baroreceptor activation device in the form of a transducer which mechanically induces a baroreceptor signal in accordance with an embodiment of the present invention.

Refer now to FIG. 11 which shows a baroreceptor activation device 240 in the form of one or more transducers 242. Preferably, the transducers 242 comprise an array surrounding the vascular wall. The transducers 242 may be intravascularly or extravascularly positioned adjacent to the baroreceptors 30. In this embodiment, the transducers 242 comprise devices which convert electrical signals into some physical phenomena, such as mechanical vibration or acoustic waves. The electrical signals are provided to the transducers 242 by way of electrical cables 244 which are connected to the driver 66 of the control system 60. By selectively activating the transducers 242 to create a physical phenomena, the baroreceptors 30 may be mechanically activated.

The transducers 242 may comprise an acoustic transmitter which transmits sonic or ultrasonic sound waves into the vascular wall 40 to activate the baroreceptors 30. Alternatively, the transducers 242 may comprise a piezoelectric material which vibrates the vascular wall to activate the baroreceptors 30. As a further alternative, the transducers 242 may comprise an artificial muscle which deflects upon application of an electrical signal. An example of an artificial muscle transducer comprises plastic impregnated with a lithium-perchlorate electrolyte disposed between sheets of polypyrrole, a conductive polymer. Such plastic muscles may be electrically activated to cause deflection in different directions depending on the polarity of the applied current.

Figure 12:
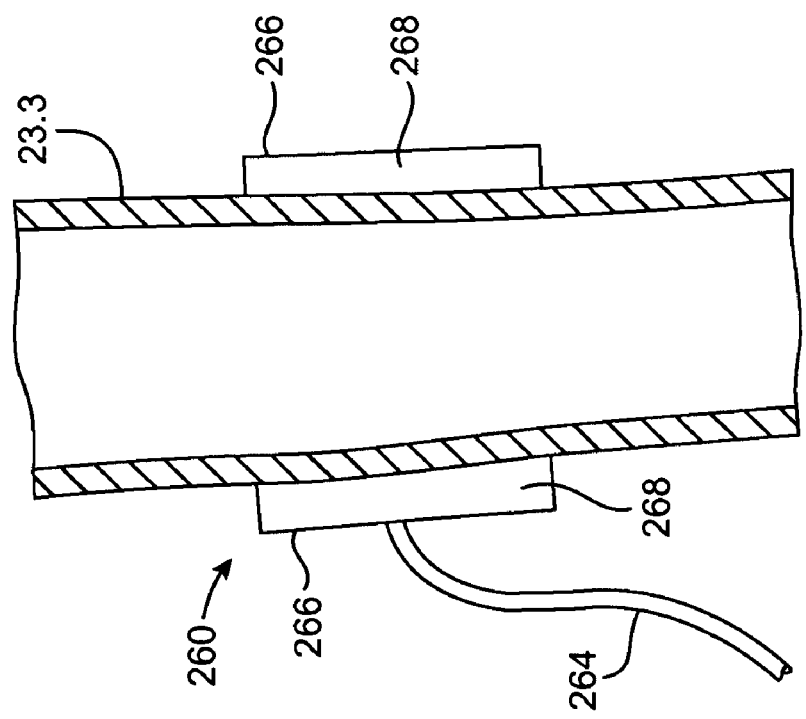
FIG. 12 is a schematic illustration of a baroreceptor activation device in the form of a fluid delivery device which may be used to deliver an agent which chemically or biologically induces a baroreceptor signal in accordance with an embodiment of the present invention.

Refer now to FIG. 12 which shows a baroreceptor activation device 260 in the form of a local fluid delivery device 262 suitable for delivering a chemical or biological fluid agent to the vascular wall adjacent the baroreceptors 30. The local fluid delivery device 262 may be located intravascularly, extravascularly, or intramurally. For purposes of illustration only, the local fluid delivery device 262 is positioned extravascularly.

The local fluid delivery device 262 may include proximal and distal seals 266 which retain the fluid agent disposed in the lumen or cavity 268 adjacent to vascular wall. Preferably, the local fluid delivery device 262 completely surrounds the vascular wall 40 to maintain an effective seal. Those skilled in the art will recognize that the local fluid delivery device 262 may comprise a wide variety of implantable drug delivery devices or pumps known in the art.

The local fluid delivery device 260 is connected to a fluid line 264 which is connected to the driver 66 of the control system 60. In this embodiment, the driver 66 comprises a pressure/vacuum source and fluid reservoir containing the desired chemical or biological fluid agent. The chemical or biological fluid agent may comprise a wide variety of stimulatory substances. Examples include veratridine, bradykinin, prostaglandins, and related substances. Such stimulatory substances activate the baroreceptors 30 directly or enhance their sensitivity to other stimuli and therefore may be used in combination with the other baroreceptor activation devices described herein. Other examples include growth factors and other agents that modify the function of the baroreceptors 30 or the cells of the vascular tissue surrounding the baroreceptors 30 causing the baroreceptors 30 to be activated or causing alteration of their responsiveness or activation pattern to other stimuli. It is also contemplated that injectable stimulators that are induced remotely, as described in U.S. Pat. No. 6,061,596 which is incorporated herein by reference, may be used with the present invention.

As an alternative, the fluid delivery device 260 may be used to deliver a photochemical that is essentially inert until activated by light to have a stimulatory effect as described above. In this embodiment, the fluid delivery device 260 would include a light source such as a light emitting diode (LED), and the driver 66 of the control system 60 would include a pulse generator for the LED combined with a pressure/vacuum source and fluid reservoir described previously. The photochemical would be delivered with the fluid delivery device 260 as described above, and the photochemical would be activated, deactivated or modulated by activating, deactivating or modulating the LED.

As a further alternative, the fluid delivery device 260 may be used to deliver a warm or hot fluid (e.g. saline) to thermally activate the baroreceptors 30. In this embodiment, the driver 66 of the control system 60 would include a heat generator for heating the fluid, combined with a pressure/vacuum source and fluid reservoir described previously. The hot or warm fluid would be delivered and preferably circulated with the fluid delivery device 260 as described above, and the temperature of the fluid would be controlled by the driver 66.

Figure 13:
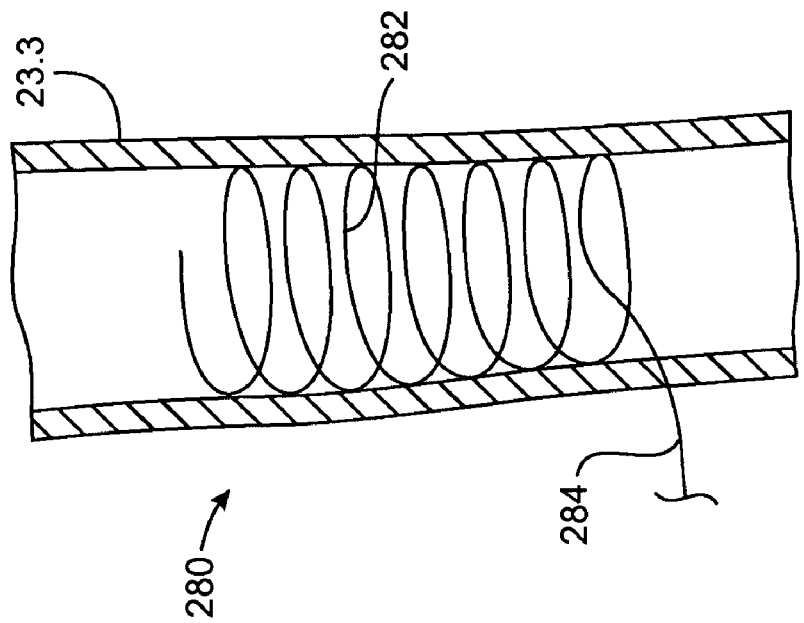
FIG. 13 is a schematic illustration of a baroreceptor activation device in the form of an internal conductive structure which electrically or thermally induces a baroreceptor signal in accordance with an embodiment of the present invention.

Refer now to FIG. 13 which shows a baroreceptor activation device 280 in the form of an intravascular electrically conductive structure or electrode 282. The electrode structure 282 may comprise a self-expanding or balloon expandable coil, braid or other stent-like structure disposed in the vascular lumen. The electrode structure 282 may serve the dual purpose of maintaining lumen patency while also delivering electrical stimuli. To this end, the electrode structure 282 may be implanted utilizing conventional intravascular stent and filter delivery techniques. Preferably, the electrode structure 282 comprises a geometry which allows blood perfusion therethrough. The electrode structure 282 comprises electrically conductive material which may be selectively insulated to establish contact with the inside surface of the vascular wall 40 at desired locations, and limit extraneous electrical contact with blood flowing through the vessel and other tissues.

The electrode structure 282 is connected to electric lead 284 which is connected to the driver 66 of the control system 60. The driver 66, in this embodiment, may comprise a power amplifier, pulse generator or the like to selectively deliver electrical control signals to structure 282. As mentioned previously, the electrical control signal generated by the driver 66 may be continuous, periodic, episodic or a combination thereof, as dictated by an algorithm contained in memory 62 of the control system 60. Continuous control signals include a constant pulse, a constant train of pulses, a triggered pulse and a triggered train of pulses. Periodic control signals include each of the continuous control signals described above which have a designated start time and a designated duration. Episodic control signals include each of the continuous control signals described above which are triggered by an episode.

By selectively activating, deactivating or otherwise modulating the electrical control signal transmitted to the electrode structure 282, electrical energy may be delivered to the vascular wall to activate the baroreceptors 30. As discussed previously, activation of the baroreceptors 30 may occur directly or indirectly. In particular, the electrical signal delivered to the vascular wall 40 by the electrode structure 282 may cause the vascular wall to stretch or otherwise deform thereby indirectly activating the baroreceptors 30 disposed therein.

Alternatively, the electrical signals delivered to the vascular wall by the electrode structure 282 may directly activate the baroreceptors 30 by changing the electrical potential across the baroreceptors 30. In either case, the electrical signal is delivered to the vascular wall 40 immediately adjacent to the baroreceptors 30. It is also contemplated that the electrode structure 282 may delivery thermal energy by utilizing a semi-conductive material having a higher resistance such that the electrode structure 282 resistively generates heat upon application of electrical energy.

Various alternative embodiments are contemplated for the electrode structure 282, including its design, implanted location, and method of electrical activation. For example, the electrode structure 282 may be unipolar as shown in FIG. 13 using the surrounding tissue as ground, or bipolar using leads connected to either end of the structure 282 as shown in FIGS. 23A and 23B. In the embodiment of FIGS. 23A and 23B, the electrode structure 282 includes two or more individual electrically conductive members 283/285 which are electrically isolated at their respective cross-over points utilizing insulative materials. Each of the members 283/285 is connected to a separate conductor contained within the electrical lead 284. Alternatively, an array of bipoles may be used as described in more detail with reference to FIGS. 21A-21C. As a further alternative, a multipolar arrangement may be used wherein three or more electrically conductive members are included in the structure 282. For example, a tripolar arrangement may be provided by one electrically conductive member having a polarity disposed between two electrically conductive members having the opposite polarity.

Figure 21B:
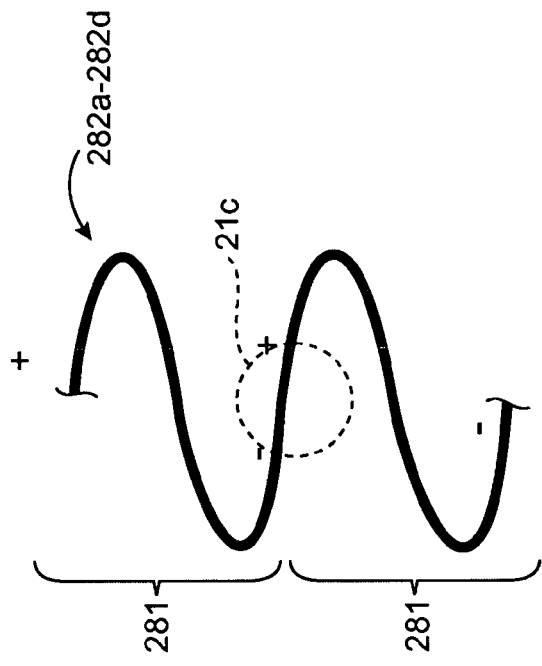
FIGS. 21A-21C are schematic illustrations of a preferred embodiment of an inductively activated electrically conductive structure.
Figure 21C:
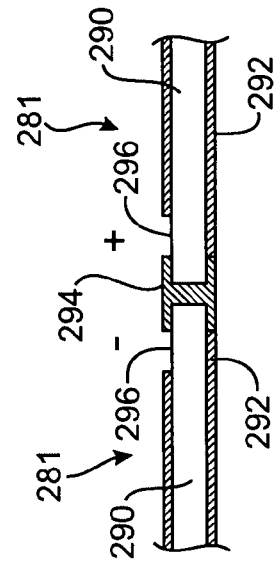
Figure 21A:
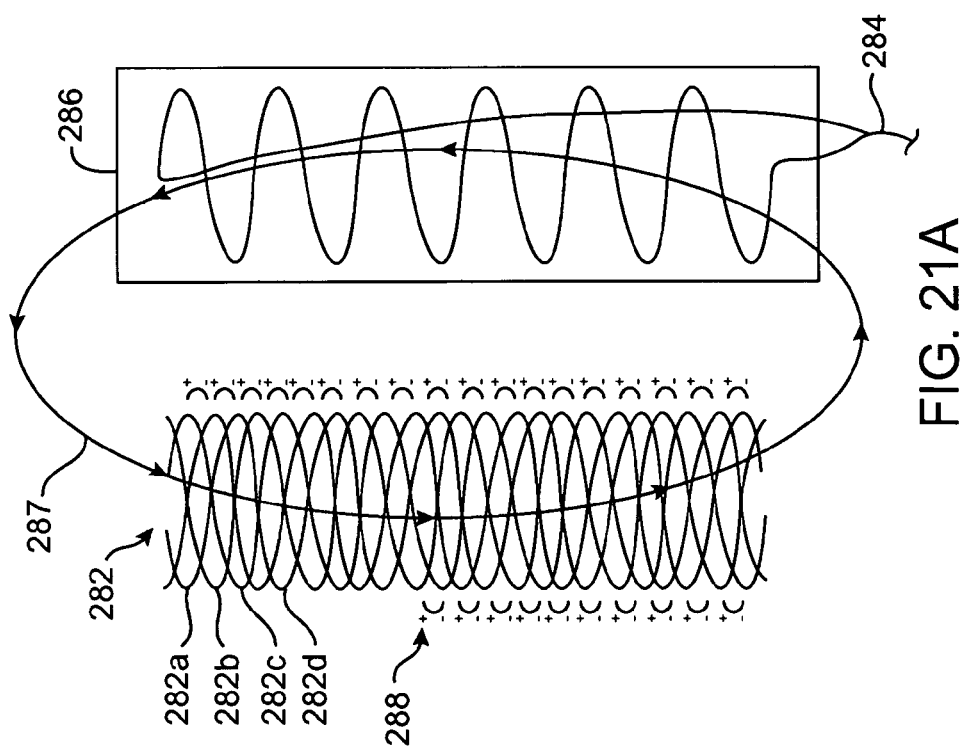

In terms of electrical activation, the electrical signals may be directly delivered to the electrode structure 282 as described with reference to FIG. 13, or indirectly delivered utilizing an inductor 286 as illustrated in FIGS. 14-16 and 21. The embodiments of FIGS. 14-16 and 21 utilize an inductor 286 which is operably connected to the driver 66 of the control system 60 by way of electrical lead 284. The inductor 286 comprises an electrical winding which creates a magnetic field 287 (as seen in FIG. 21) around the electrode structure 282. The magnetic field 287 may be alternated by alternating the direction of current flow through the inductor 286. Accordingly, the inductor 286 may be utilized to create current flow in the electrode structure 282 to thereby deliver electrical signals to the vascular wall 40 to directly or indirectly activate the baroreceptors 30. In all embodiments, the inductor 286 may be covered with an electrically insulative material to eliminate direct electrical stimulation of tissues surrounding the inductor 286. A preferred embodiment of an inductively activated electrode structure 282 is described in more detail with reference to FIGS. 21A-21C.

Figure 15:
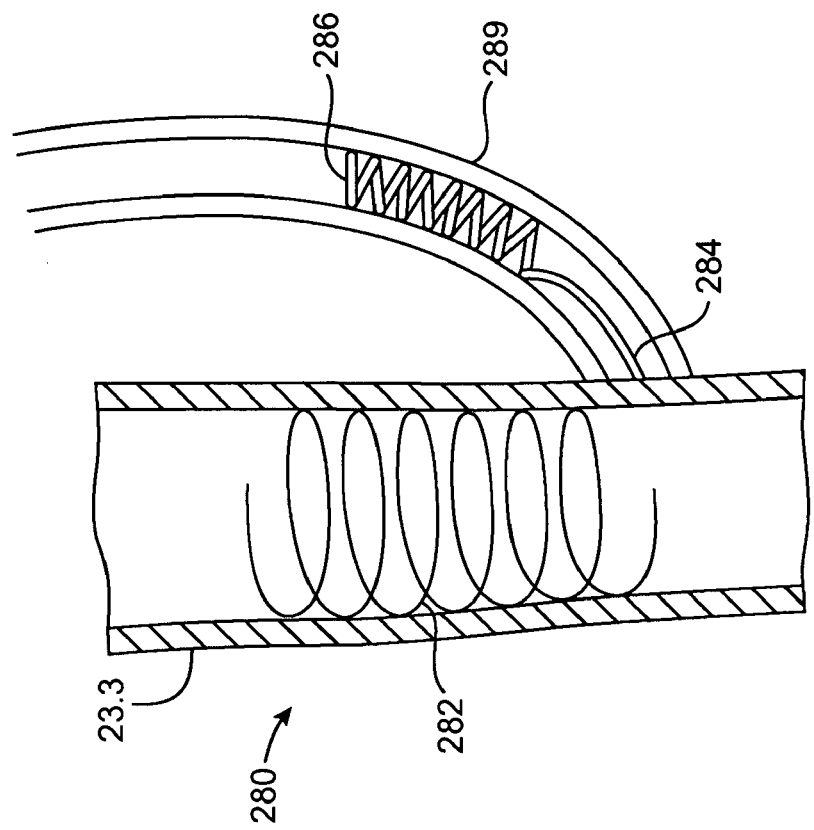
FIG. 15 is a schematic illustration of a baroreceptor activation device in the form of an internal conductive structure, activated by an internal inductor located in an adjacent vessel, which electrically or thermally induces a baroreceptor signal in accordance with an embodiment of the present invention.
Figure 14:
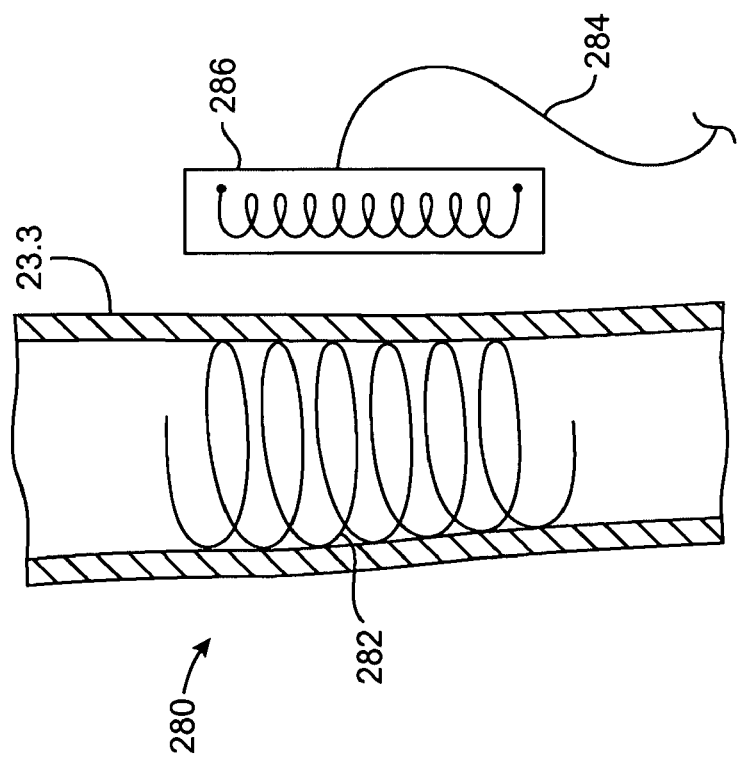
FIG. 14 is a schematic illustration of a baroreceptor activation device in the form of an internal conductive structure, activated by an internal inductor, which electrically or thermally induces a baroreceptor signal in accordance with an embodiment of the present invention.

The embodiments of FIGS. 13-16 may be modified to form a cathode/anode arrangement. Specifically, the electrical inductor 286 would be connected to the driver 66 as shown in FIGS. 14-16 and the electrode structure 282 would be connected to the driver 66 as shown in FIG. 13. With this arrangement, the electrode structure 282 and the inductor 286 may be any suitable geometry and need not be coiled for purposes of induction. The electrode structure 282 and the inductor 286 would comprise a cathode/anode or anode/cathode pair. For example, when activated, the cathode 282 may generate a primary stream of electrons which travel through the inter-electrode space (i.e., vascular tissue and baroreceptors 30) to the anode 286. The cathode is preferably cold, as opposed to thermionic, during electron emission. The electrons may be used to electrically or thermally activate the baroreceptors 30 as discussed previously.

The electrical inductor 286 is preferably disposed as close as possible to the electrode structure 282. For example, the electrical inductor 286 may be disposed adjacent the vascular wall as illustrated in FIG. 14. Alternatively, the inductor 286 may be disposed in an adjacent vessel 289 as illustrated in FIG. 15. If the electrode structure 282 is disposed in the carotid sinus 20, for example, the inductor 286 may be disposed in the internal jugular vein 21 as illustrated in FIG. 15. In the embodiment of FIG. 15, the electrical inductor 286 may comprise a similar structure as the electrode structure 282. As a further alternative, the electrical inductor 286 may be disposed outside the patient's body, but as close as possible to the electrode structure 282. If the electrode structure 282 is disposed in the carotid sinus 20, for example, the electrical inductor 286 may be disposed on the right or left side of the neck of the patient as illustrated in FIG. 16. In the embodiment of FIG. 16, wherein the electrical inductor 286 is disposed outside the patient's body, the control system 60 may also be disposed outside the patient's body.

In terms of implant location, the electrode structure 282 may be intravascularly disposed as described with reference to FIG. 13, or extravascularly disposed as described with reference to FIG. 17, which show schematic illustrations of a baroreceptor activation device 300 in the form of an extravascular electrically conductive structure or electrode 302. Except as described herein, the extravascular electrode structure 302 is the same in design, function, and use as the intravascular electrode structure 282. The electrode structure 302 may comprise a coil, braid or other structure capable of surrounding the vascular wall. Alternatively, the electrode structure 302 may comprise one or more electrode patches distributed around the outside surface of the vascular wall. Because the electrode structure 302 is disposed on the outside surface of the vascular wall, intravascular delivery techniques may not be practical, but minimally invasive surgical techniques will suffice. The extravascular electrode structure 302 may receive electrical signals directly from the driver 66 of the control system 60 by way of electrical lead 304, or indirectly by utilizing an inductor (not shown) as described with reference to FIGS. 14-16.

Figure 19:
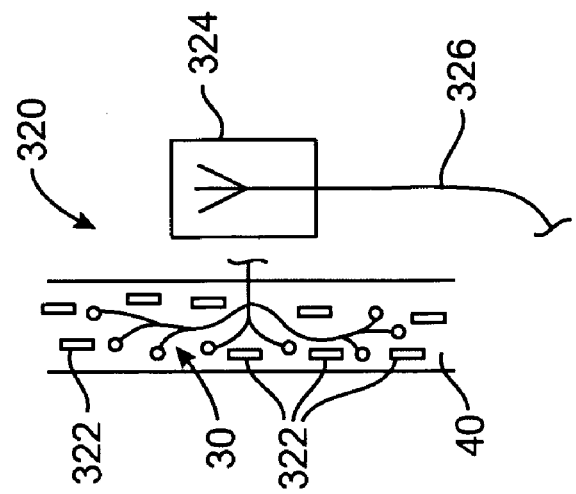
FIG. 19 is a schematic illustration of a baroreceptor activation device in the form of an electromagnetic field responsive device which electrically or thermally induces a baroreceptor signal in accordance with an embodiment of the present invention.
Figure 18:
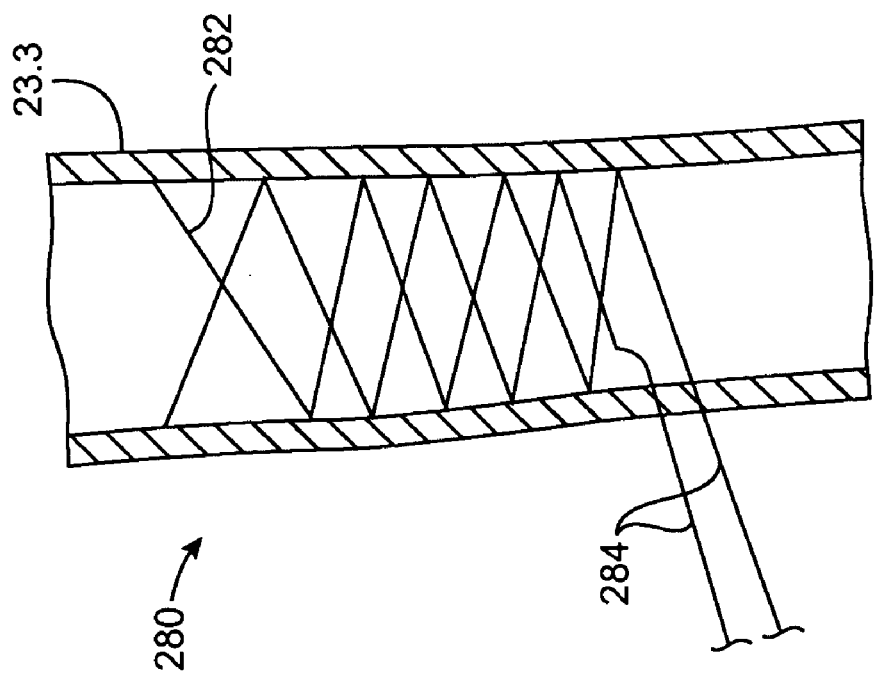
FIG. 18 is a schematic illustration of a baroreceptor activation device in the form of an internal bipolar conductive structure which electrically or thermally induces a baroreceptor signal in accordance with an embodiment of the present invention.

Refer now to FIG. 19 which shows a baroreceptor activation device 320 in the form of electrically conductive particles 322 disposed in the vascular wall. This embodiment is substantially the same as the embodiments described with reference to FIGS. 13-18, except that the electrically conductive particles 322 are disposed within the vascular wall, as opposed to the electrically conductive structures 282/302 which are disposed on either side of the vascular wall. In addition, this embodiment is similar to the embodiment described with reference to FIG. 10, except that the electrically conductive particles 322 are not necessarily magnetic as with magnetic particles 222, and the electrically conductive particles 322 are driven by an electromagnetic filed rather than by a magnetic field.

In this embodiment, the driver 66 of the control system 60 comprises an electromagnetic transmitter such as an radiofrequency or microwave transmitter. Electromagnetic radiation is created by the transmitter 66 which is operably coupled to an antenna 324 by way of electrical lead 326. Electromagnetic waves are emitted by the antenna 324 and received by the electrically conductive particles 322 disposed in the vascular wall 40. Electromagnetic energy creates oscillating current flow within the electrically conductive particles 322, and depending on the intensity of the electromagnetic radiation and the resistivity of the conductive particles 322, may cause the electrical particles 322 to generate heat. The electrical or thermal energy generated by the electrically conductive particles 322 may directly activate the baroreceptors 30, or indirectly activate the baroreceptors 30 by way of the surrounding vascular wall tissue.

The electromagnetic radiation transmitter 66 and antenna 324 may be disposed in the patient's body, with the antenna 324 disposed adjacent to the conductive particles in the vascular wall 40 as illustrated in FIG. 19. Alternatively, the antenna 324 may be disposed in any of the positions described with reference to the electrical inductor shown in FIGS. 14-16. It is also contemplated that the electromagnetic radiation transmitter 66 and antenna 324 may be utilized in combination with the intravascular and extravascular electrically conductive structures 282/302 described with reference to FIGS. 13-18 to generate thermal energy on either side of the vascular wall.

As an alternative, the electromagnetic radiation transmitter 66 and antenna 324 may be used without the electrically conductive particles 322. Specifically, the electromagnetic radiation transmitter 66 and antenna 324 may be used to deliver electromagnetic radiation (e.g., RF, microwave) directly to the baroreceptors 30 or the tissue adjacent thereto to cause localized heating, thereby thermally inducing a baroreceptor 30 signal.

Figure 20:
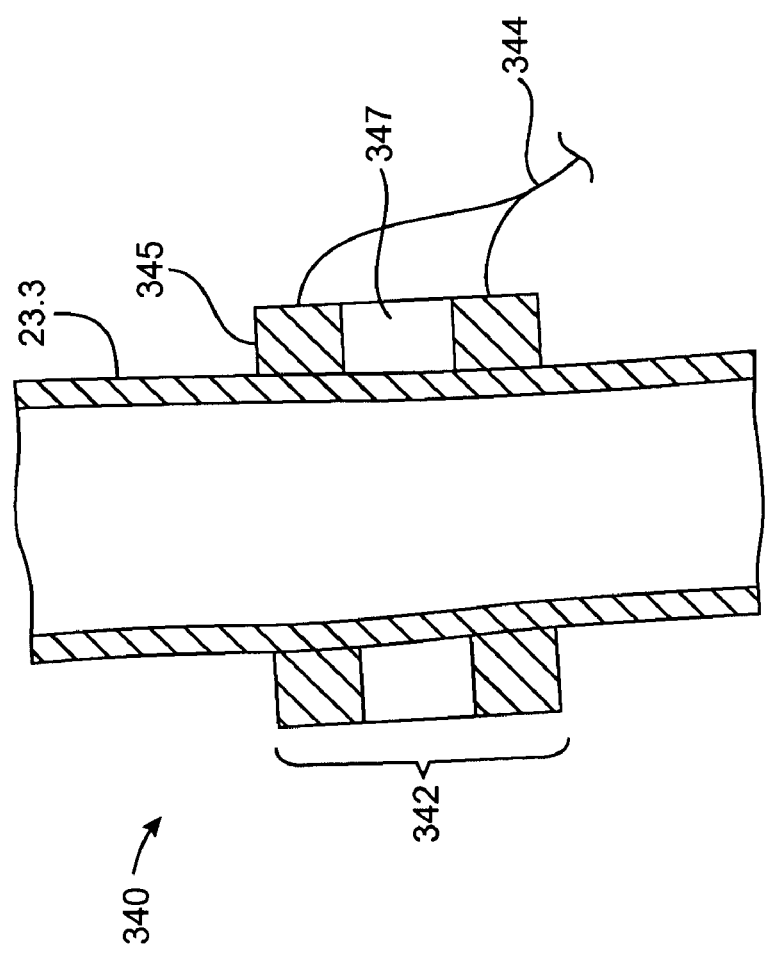
FIG. 20 is a schematic illustration of a baroreceptor activation device in the form of an external Peltier device which thermally induces a baroreceptor signal in accordance with an embodiment of the present invention.

Refer now to FIG. 20 which shows a baroreceptor activation device 340 in the form of a Peltier effect device 342. The Peltier effect device 342 may be extravascularly positioned as illustrated, or may be intravascularly positioned similar to an intravascular stent or filter. The Peltier effect device 342 is operably connected to the driver 66 of the control system 60 by way of electrical lead 344. The Peltier effect device 342 includes two dissimilar metals or semiconductors 343/345 separated by a thermal transfer junction 347. In this particular embodiment, the driver 66 comprises a power source which delivers electrical energy to the dissimilar metals or semiconductors 343/345 to create current flow across the thermal junction 347.

When current is delivered in an appropriate direction, a cooling effect is created at the thermal junction 347. There is also a heating effect created at the junction between the individual leads 344 connected to the dissimilar metals or semiconductors 343/345. This heating effect, which is proportional to the cooling effect, may be utilized to activate the baroreceptors 30 by positioning the junction between the electrical leads 344 and the dissimilar metals or semiconductors 343/345 adjacent to the vascular wall 40.

Refer now to FIGS. 21A-21C which show schematic illustrations of a preferred embodiment of an inductively activated electrode structure 282 for use with the embodiments described with reference to FIGS. 14-16. In this embodiment, current flow in the electrode structure 282 is induced by a magnetic field 287 created by an inductor 286 which is operably coupled to the driver 66 of the control system 60 by way of electrical cable 284. The electrode structure 282 preferably comprises a multi-filar self-expanding braid structure including a plurality of individual members 282a, 282b, 282c and 282d. However, the electrode structure 282 may simply comprise a single coil for purposes of this embodiment.

Each of the individual coil members 282a-282d comprising the electrode structure 282 consists of a plurality of individual coil turns 281 connected end to end as illustrated in FIGS. 21B and 21C. FIG. 21C is a detailed view of the connection between adjacent coil turns 281 as shown in FIG. 21B. Each coil turn 281 comprises electrically isolated wires or receivers in which a current flow is established when a changing magnetic field 287 is created by the inductor 286. The inductor 286 is preferably covered with an electrically insulative material to eliminate direct electrical stimulation of tissues surrounding the inductor 286. Current flow through each coil turn 281 results in a potential drop 288 between each end of the coil turn 281. With a potential drop defined at each junction between adjacent coil turns 281, a localized current flow cell is created in the vessel wall adjacent each junction. Thus an array or plurality of bipoles are created by the electrode structure 282 and uniformly distributed around the vessel wall. Each coil turn 281 comprises an electrically conductive wire material 290 surrounded by an electrically insulative material 292. The ends of each coil turn 281 are connected by an electrically insulated material 294 such that each coil turn 281 remains electrically isolated. The insulative material 294 mechanically joins but electrically isolates adjacent coil turns 281 such that each turn 281 responds with a similar potential drop 288 when current flow is induced by the changing magnetic field 287 of the inductor 286. An exposed portion 296 is provided at each end of each coil turn 281 to facilitate contact with the vascular wall tissue. Each exposed portion 296 comprises an isolated electrode in contact with the vessel wall. The changing magnetic field 287 of the inductor 286 causes a potential drop in each coil turn 281 thereby creating small current flow cells in the vessel wall corresponding to adjacent exposed regions 296. The creation of multiple small current cells along the inner wall of the blood vessel serves to create a cylindrical zone of relatively high current density such that the baroreceptors 30 are activated. However, the cylindrical current density field quickly reduces to a negligible current density near the outer wall of the vascular wall, which serves to limit extraneous current leakage to minimize or eliminate unwanted activation of extravascular tissues and structures such as nerves or muscles.

To address low blood pressure and other conditions requiring blood pressure augmentation, some of the baroreceptor activation devices described previously may be used to selectively and controllably regulate blood pressure by inhibiting or dampening baroreceptor signals. By selectively and controllably inhibiting or dampening baroreceptor signals, the present invention reduces conditions associated with low blood pressure as described previously. Specifically, the present invention would function to increase the blood pressure and level of sympathetic nervous system activation by inhibiting or dampening the activation of baroreceptors.

This may be accomplished by utilizing mechanical, thermal, electrical and chemical or biological means. Mechanical means may be triggered off the pressure pulse of the heart to mechanically limit deformation of the arterial wall. For example, either of the external compression devices 120/160 described previously may be used to limit deformation of the arterial wall. Alternatively, the external compression device may simply limit diametrical expansion of the vascular wall adjacent the baroreceptors without the need for a trigger or control signal.

Thermal means may be used to cool the baroreceptors 30 and adjacent tissue to reduce the responsiveness of the baroreceptors 30 and thereby dampen baroreceptor signals. Specifically, the baroreceptor 30 signals may be dampened by either directly cooling the baroreceptors 30, to reduce their sensitivity, metabolic activity and function, or by cooling the surrounding vascular wall tissue thereby causing the wall to become less responsive to increases in blood pressure. An example of this approach is to use the cooling effect of the Peltier device 340. Specifically, the thermal transfer junction 347 may be positioned adjacent the vascular wall to provide a cooling effect. The cooling effect may be used to dampen signals generated by the baroreceptors 30. Another example of this approach is to use the fluid delivery device 260 to deliver a cool or cold fluid (e.g. saline). In this embodiment, the driver 66 would include a heat exchanger to cool the fluid and the control system 60 may be used to regulate the temperature of the fluid, thereby regulating the degree of baroreceptor 30 signal dampening.

Electrical means may be used to inhibit baroreceptor 30 activation by, for example, hyperpolarizing cells in or adjacent to the baroreceptors 30. Examples of devices and method of hyperpolarizing cells are disclosed in U.S. Pat. No. 5,814,079 to Kieval, and U.S. Pat. No. 5,800,464 to Kieval, the entire disclosures of which are hereby incorporated by reference. Such electrical means may be implemented using any of the embodiments discussed with reference to FIGS. 13-18 and 21.

Chemical or biological means may be used to reduce the sensitivity of the baroreceptors 30. For example, a substance that reduces baroreceptor sensitivity may be delivered using the fluid delivery device 260 described previously. The desensitizing agent may comprise, for example, tetrodotoxin or other inhibitor of excitable tissues. From the foregoing, it should be apparent to those skilled in the art that the present invention provides a number of devices, systems and methods by which the blood pressure, nervous system activity, and neurohormonal activity may be selectively and controllably regulated by activating baroreceptors or by inhibiting/dampening baroreceptor signals. Thus, the present invention may be used to increase or decrease blood pressure, sympathetic nervous system activity and neurohormonal activity, as needed to minimize deleterious effects on the heart, vasculature and other organs and tissues.

The baroreceptor activation devices described previously may also be used to provide antiarrhythmic effects. It is well known that the susceptibility of the myocardium to the development of conduction disturbances and malignant cardiac arrhythmias is influenced by the balance between sympathetic and parasympathetic nervous system stimulation to the heart. That is, heightened sympathetic nervous system activation, coupled with decreased parasympathetic stimulation, increases the irritability of the myocardium and likelihood of an arrhythmia. Thus, by decreasing the level of sympathetic nervous system activation and enhancing the level of parasympathetic activation, the devices, systems and methods of the current invention may be used to provide a protective effect against the development of cardiac conduction disturbances.

For each of these applications, it may be desirable to focus the output of the activation device 70 on portions of the carotid sinus 20 that are rich in baroreceptors 30, and minimize the output delivered to portions of the carotid sinus 20 with fewer or no baroreceptors 30. By focusing the output as such, baroreceptor activation may be maximized and the required device output (i.e., the required power or energy output of the baroreceptor activation device 70) may be minimized. In particular, the ratio of baroreceptor activation to device output (A/O) may be maximized. In addition, by focusing the output as such, extraneous tissue activation may be minimized, power consumption (by the device 70) may minimized, and the degradation rate of baroreceptor responsiveness may be minimized.

It has been found that the A/O ratio is a function of the position of the baroreceptor activation device. In particular, it has been found that the A/O ratio varies about the circumference of the carotid artery near the carotid sinus 20, perhaps due to variations in the location or density of baroreceptors. Although described herein with reference to the carotid sinus 20, it is also likely that the A/O ratio varies at all of the anatomical locations which contain baroreceptors as described previously.

In order to position the baroreceptor activation device 70 to maximize the A/O ratio, a mapping technique may be employed. For example, the device 70 may be oriented in two or more different positions and/or at two or more different anatomical locations. More specifically, the output means of the device 70 may be disposed in two or more different positions/locations. The output means generally refers to the structure through which the stimulus is transferred to the tissue surrounding the baroreceptors. In electrical activation embodiments, for example, the output means may comprise electrodes.

At each position/location, the device 70 may be activated to a specified level, and the degree of baroreceptor activation may be observed or measured. The degree of baroreceptor activation may be inferentially determined by measuring changes in heart rate, blood pressure, and/or other physiological parameters indicative of baroreceptor activation. The resulting measurements may be used to generate an A/O ratio for each position/location. The A/O ratios for each location may be graphically plotted to generate a map. The A/O ratios may be compared, and the position/location having the most desirable A/O ratio may be selected for the device 70.

EXPERIMENTAL

Figure 22A:
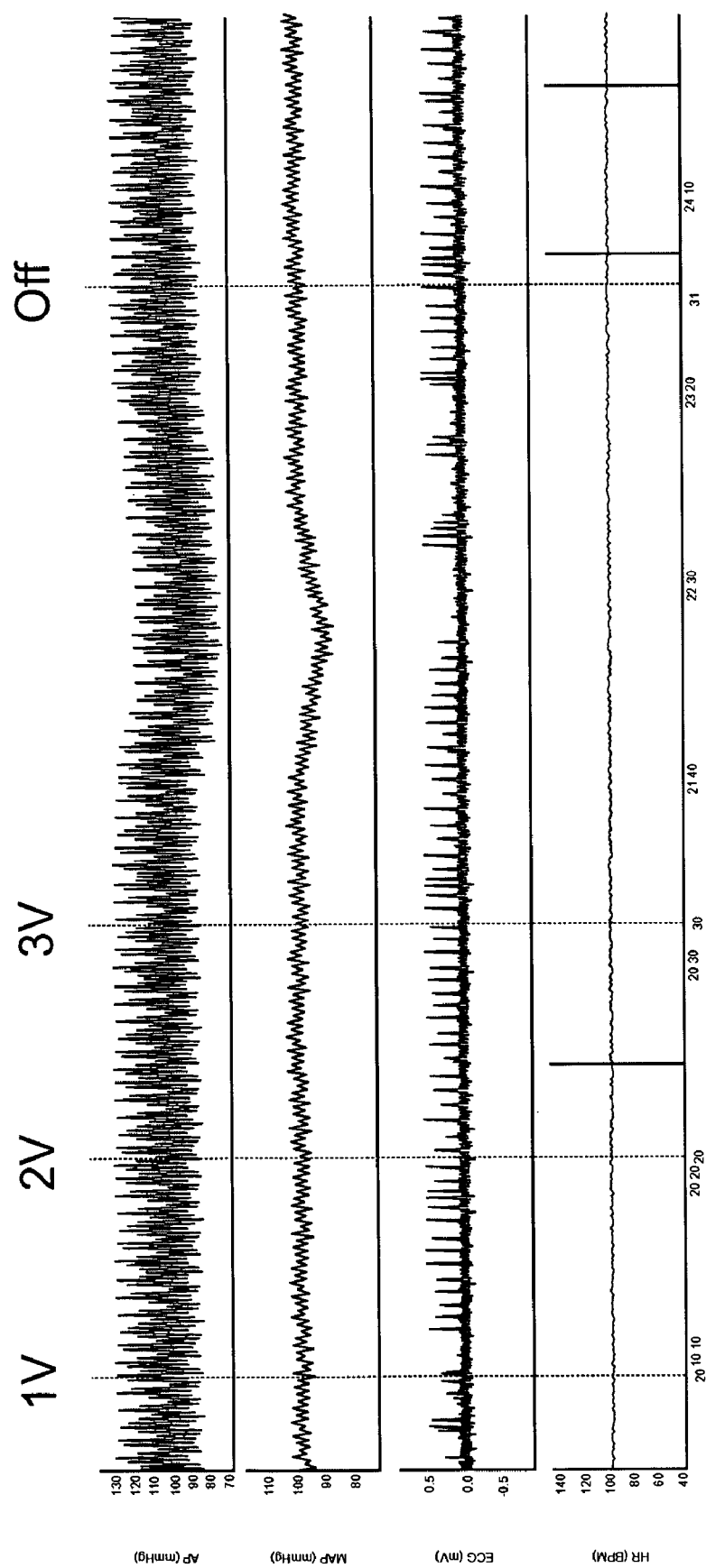
FIGS. 22A-22C are ECG charts of a dog undergoing stimulation of the abdominal IVC.
Figure 22B:
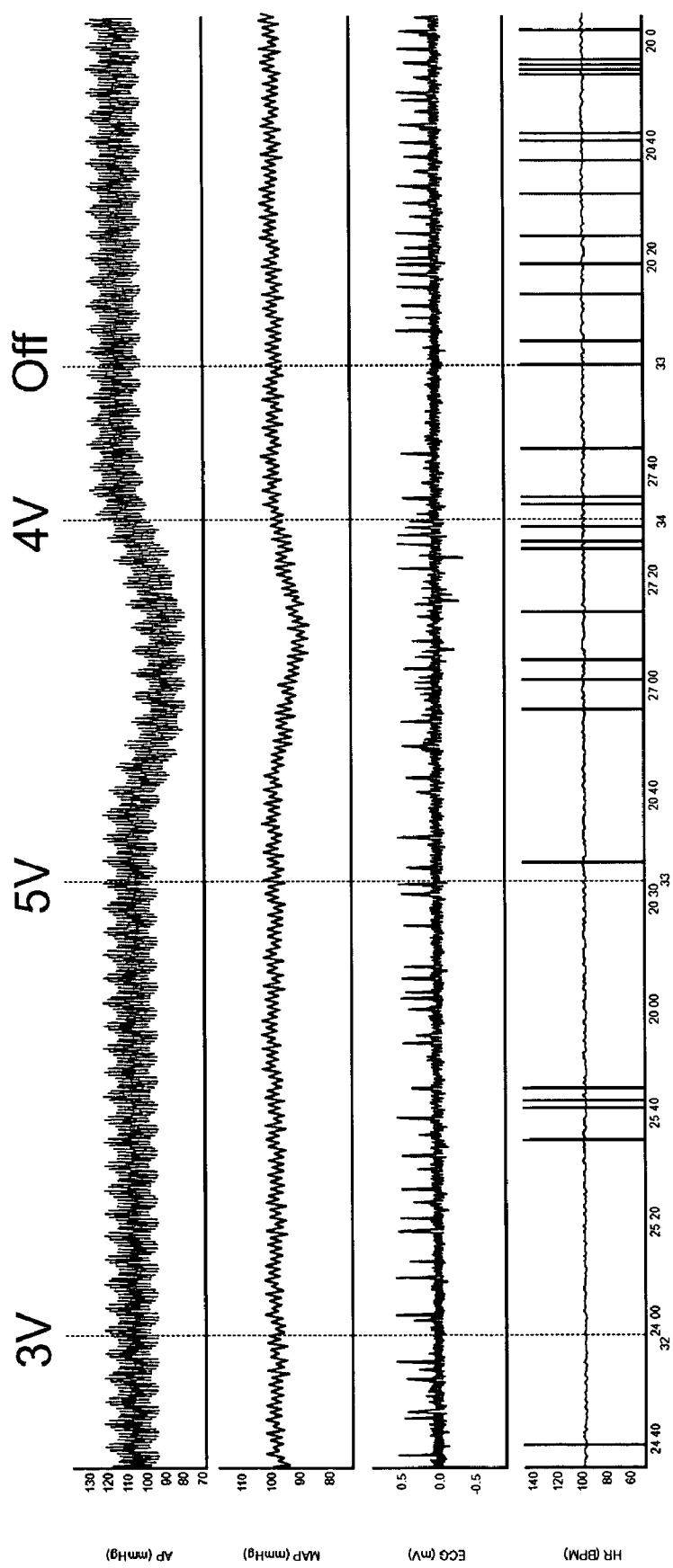
Figure 22C:
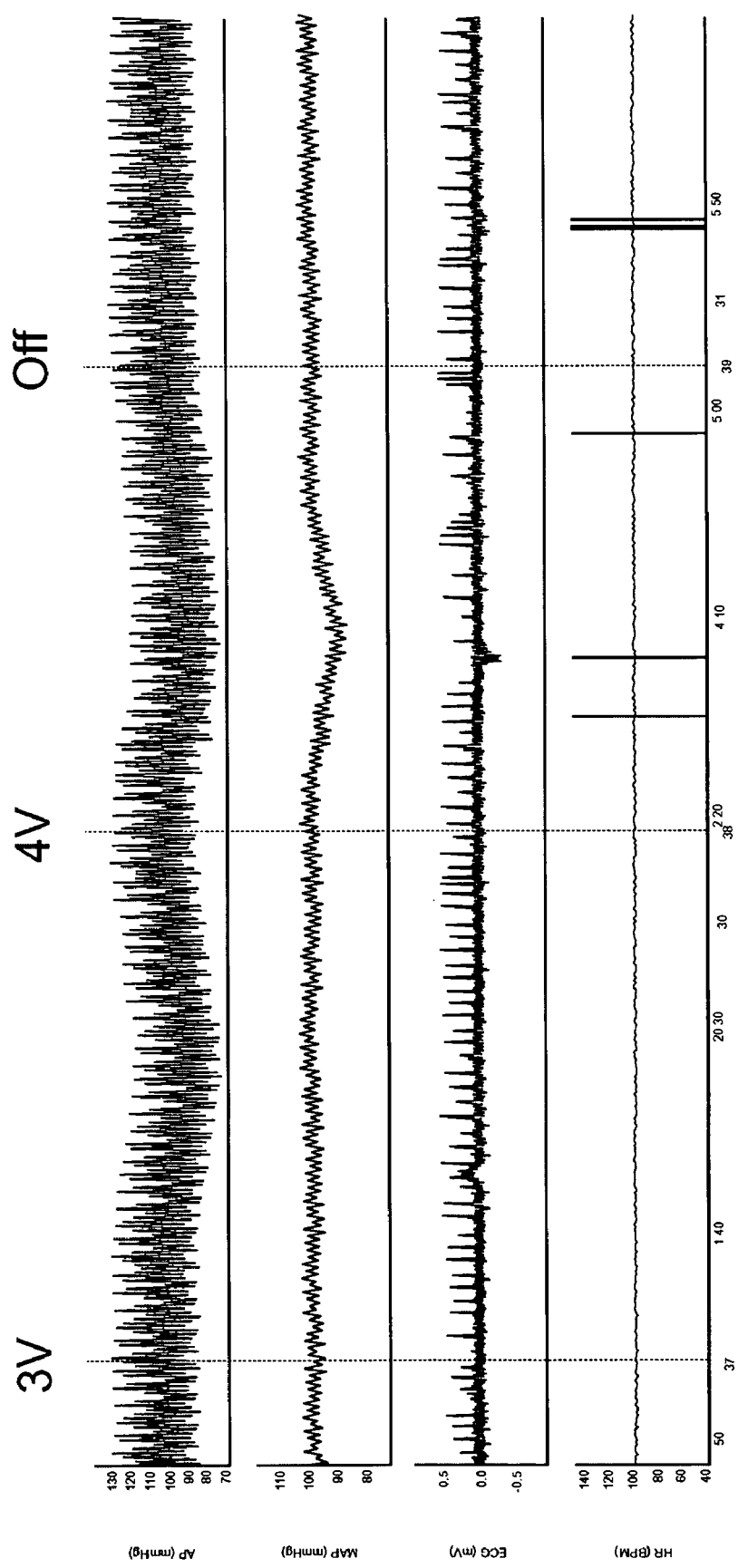

An electrode system was introduced into the inferior vena cava of an anesthetized dog. The electrode system was an eight lead, 64-electrode 8F Constellation® catheter from Boston Scientific EP Technologies, Sunnyvale, Calif. The electrode system was placed endovascularly in the abdominal vena cava. The electrode system was activated using trains of electrical impulses of 0-6 volts, a frequency of 100 hz, and a pulse width of 0.5 ms. During various activation experiments, arterial pressure, mean arterial pressure and heart rate were monitored. The results of three experiments are shown in FIGS. 22A-C. These figures demonstrate a change in blood pressure as energy is applied to the vessel wall, with recovery to pre-activation levels when the energy is discontinued.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. An apparatus comprising:
   a flexible lead body extending from a proximal end to a distal end;
   an expandable electrode coupled to the lead body, the expandable electrode comprising a plurality of electrically conductive members, each electrically conductive member coupled to a separate conductor within the lead body; and
   an implantable pulse generator electrically coupled to the electrode via the separate conductors, the implantable pulse generator programmed to selectively activate each electrically conductive member of the electrode and determine a resulting degree of baroreceptor activation, and further programmed to deliver a baroreflex stimulation signal directly to a baroreceptor in a pulmonary artery via at least one of the electrically conductive members of the expandable electrode based on the determined degree of baroreceptor activation.

2. The apparatus of claim 1, wherein the pulse generator delivers at least a 10 hertz pulse train via the electrode.

3. The apparatus of claim 1, wherein the expandable electrode is adapted to fix the flexible lead body in place by frictional forces.

4. The apparatus of claim 1, wherein the expandable electrode includes a spiral configuration.

5. The apparatus of claim 1, wherein the expandable electrode is adapted to be chronically implanted in the pulmonary artery.

6. The apparatus of claim 1, wherein the flexible lead body further includes a sensor adapted to monitor blood pressure.

7. An apparatus comprising:
   a flexible lead body extending from a proximal end to a distal end;
   an expandable electrode coupled proximate the distal end, the expandable electrode having a stent-like structure and an expanded diameter dimensioned to abut a wall of a pulmonary artery, the expandable electrode comprising a plurality of electrically conductive members, each electrically conductive member individually coupled to a separate conductor of the lead body; and
   an implantable pulse generator electrically coupled to the expandable electrode via the conductors, wherein the implantable pulse generator is programmed to deliver an activation signal to each of the plurality of electrically conductive members and determine a degree of baroreceptor activation resulting from each activation signal, the implantable pulse generator further programmed to deliver a baroreflex stimulation signal to a baroreceptor in the pulmonary artery via at least one electrically conductive member of the expandable electrode based on the determined degree of baroreceptor activation, wherein the implantable pulse generator is programmed such that the signal is delivered for a duration, at a voltage and a pulse frequency and a pulse width in a range that causes the lowering of blood pressure.

8. The apparatus of claim 7, wherein the expandable electrode is adapted to fix the flexible lead body in place by frictional forces.

9. The apparatus of claim 7, wherein the expandable electrode is adapted to be chronically implanted in the pulmonary artery.

10. The apparatus of claim 7, wherein the flexible lead body further includes a sensor adapted to monitor blood pressure.

* * * * *